United States Patent

Bugaut et al.

[11] 4,330,291
[45] May 18, 1982

[54] NITRATED COUPLER COMPOUNDS USEFUL IN DIRECT DYEING AND SIMULTANEOUS OXIDATION AND DIRECT DYEING OF KERATINIC FIBERS

[76] Inventors: Andrée Bugaut, 7, rue des Abondances, 92100 Boulogne-Billancourt; Ginette Jeanminet, 21, rue du Commandant Brasseur, 93600 Aulnay-sous-Bois, both of France

[21] Appl. No.: 127,461

[22] Filed: Mar. 5, 1980

Related U.S. Application Data

[63] Continuation of Ser. No. 698,126, Jun. 21, 1976, abandoned.

[30] Foreign Application Priority Data

Jun. 26, 1975 [FR] France .................... 75 20155
Nov. 7, 1975 [FR] France .................... 75 34208

[51] Int. Cl.³ .................................. A61K 7/13
[52] U.S. Cl. .................................. 8/406; 8/407; 8/408; 8/409; 8/410; 8/412; 8/414; 8/416; 8/421; 8/423
[58] Field of Search .................. 8/406, 407, 408, 409, 8/410, 412, 414, 416, 421, 423

[56] References Cited

U.S. PATENT DOCUMENTS 3,488,138  1/1970  Iscowitz .................... 8/414

Primary Examiner—Donald B. Moyer
Attorney, Agent, or Firm—Cushman, Darby & Cushman

[57] ABSTRACT

A cosmetic composition for application to the hair contains either (a) at least one compound having the formula

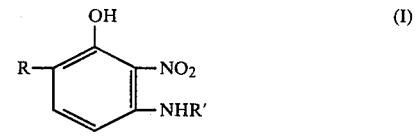

wherein:
R is hydrogen, alkyl or halogen; and
R' is hydrogen, alkyl, hydroxyalkyl, carbamylalkyl, mesylaminoalkyl, aminoalkyl, acylaminoalkyl, monoalkylaminoalkyl, dialkylaminoalkyl, piperidinoalkyl, morpholinoalkyl, carbamoyl, acyl or carbalkoxy; or (b) at least one of said compounds having formula I above and at least one benzene or heterocyclic oxidation base. The invention also relates to new couplers of formula I as well as to new indo compounds which result from the coupling of said compounds with an oxidation base. These cosmetic compositions for application to the hair are useful in direct dyeing, oxidation dyeing or simultaneous oxidation and direct dyeing of said hair.

11 Claims, No Drawings

NITRATED COUPLER COMPOUNDS USEFUL IN DIRECT DYEING AND SIMULTANEOUS OXIDATION AND DIRECT DYEING OF KERATINIC FIBERS

This is a continuation, of application Ser. No. 698,126 filed June 21, 1976, now abandoned.

The present invention relates to the dyeing of keratinic fibers particularly living human hair using compounds which are employed as direct dyes or as a coupler in oxidation dyeing procedures. These compounds are substituted 2-nitro meta-amino phenols.

It is known, for instance, from French Pat. No. 2,180,651, that nitrated phenols are capable of being employed both as a direct dye and as a component in an oxidation dyeing operation. However, the structure of the compounds of the present invention is different from that of the compounds of said French patent, and properties of the compounds of the present invention which are examined hereafter are very advantageous. Moreover, 2-nitro-3-amino phenol is also a known compound, its preparation being set forth in J. Chemical Society (C 1937, p. 1055). However, there is no mention in this publication of its dyeing characteristics.

As their name indicates, direct dyes are colored compounds used as such in dye compositions, and they participate neither in a simple oxidation nor in an oxidative condensation reaction. On the other hand, oxidation dyes result from the condensation of (1) an aromatic or heterocyclic compound possessing either amino or hydroxy groups in para or ortho position relative to one another, which are termed oxidation bases and (2) aromatic or heterocyclic compounds possessing amino or hydroxy groups in meta position relative to one another which are termed couplers. The oxidation bases and couplers are generally colorless or weakly colored compounds which yield on condensation, in the presence of an oxidizing agent, a composition useful for obtaining a permanent coloration of keratinic fibers. This composition can be prepared at the moment of use, or even in situ by the successive application of a composition containing the coupler and another composition containing the oxidation base, or vice versa. The dyeing composition thus obtained is in reality a mixture containing, in addition to the colored condensation product, some non-condensed bases or couplers, and more often than not excess oxidizing agent which is capable of continuing to react on the compounds contained in the said composition.

Generally couplers cannot be used alone as a dye. Further, they often lack stability in oxidation compositions containing an alkaline agent. Moreover, most nitrated couplers of the benzene series, if they possess their own color, they often do not couple with a desired oxidation base or they couple only partially or only very slightly therewith.

The present invention which overcomes the above disadvantages relates to a dye composition for keratinic fibers which, from the fact that this composition contains a coupler having its own color characteristics and that this coupler is sufficiently stable in an ammoniacal medium, in an alcoholic medium and a hydroalcoholic medium, is capable of being employed, either in direct dyeing procedures or in oxidation dyeing procedures in the presence of an oxidation base, or simultaneously in an oxidation and direct dyeing procedure when excess coupler is employed. Moreover, the compositions of the present invention employing an ammoniacal medium containing the couplers of the invention exhibit very good stability and storage characteristics in vats or bottles.

Furthermore, those prior nitrated compounds which have been known in a general way as couplers do not in fact constitute true couplers for the dyeing of hair, for their speed of coupling is too weak to be effectively employed as a coupler.

The composition of the present invention contains in an aqueous medium either (a) at least one compound having the formula

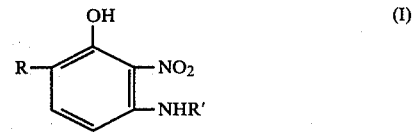

wherein

R is selected from the group consisting of hydrogen, alkyl and halogen; and

R' is selected from the group consisting of hydrogen, alkyl, hydroxyalkyl, carbamylalkyl, mesylaminoalkyl, aminoalkyl, acylaminoalkyl, monoalkylaminoalkyl, dialkylaminoalkyl, piperidinoalkyl, morpholinoalkyl, carbamoyl, acyl or carbalkoxy; or (b) at least one compound of formula (I) and at least one oxidation base selected from the group consisting of a compound having the formula

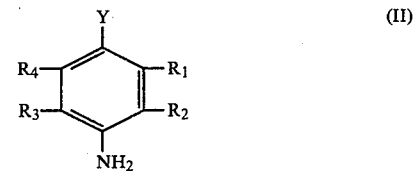

wherein $R_1$, $R_2$, $R_3$ and $R_4$ each independently are selected from the group consisting of hydrogen, alkyl, halogen and alkoxy;

Y is selected from the group consisting of hydroxyl and $-NR_5R_6$ wherein $R_5$ and $R_6$ each independently are selected from the group consisting of hydrogen, alkyl, hydroxyalkyl, carbamylalkyl, mesylaminoalkyl, aminoalkyl, acylaminoalkyl, sulfoalkyl, morpholinoalkyl, piperidinoalkyl, and a heterocyclic compound carrying on the ring thereof in para position either two amino groups, or an amino group and a hydroxy group. This oxidation base can be present in the form of a free base as the the acid addition salt thereof, such as the hydrochloride, hydroaromide or sulfate thereof. The alkyl and alkoxy moieties of the substituents defined above in formulas I and II contain from 1-4 carbon atoms.

The compounds of formula (I) when used alone in the dyeing of keratinic fibers impart to said fibers shades which are situated in the range of orange and pink as indicated in Examples T1, T2, T5 and T3. These compounds, however, can also easily be employed in combination with other direct dyes such as anthraquinone dyes, azo dyes, and nitrated dyes such as the derivatives of nitroparaphenylenediamine, indophenols, indamines and indoanilines.

In the situation where the dye composition of the present invention contains both a compound of formula (I) and a compound of formula (II), and if the said dye composition also includes a molar excess of coupler (I) relative to the quantity of base (II), the compounds of formula (I) play the role both of a direct dye and as a coupler in an oxidation dyeing operation. Thus the compounds of formula (I) react in an alkaline medium and are oxidized with the oxidation bases indicated above, to give rise at the interior of the fiber colored molecules which can be an indophenol or indoaniline depending upon the nature of the particular oxidation base employed.

If the dye composition of the present invention contains a coupler and an oxidation base in stoichiometric quantities or even if the said composition contains excess oxidation base relative to the said coupler a conventional type oxidation dyeing composition is produced.

Representative couplers of formula (I) which are particularly interesting include the following:
2-methyl-5-amino-6-nitro phenol,
2-methyl-5-N-β-hydroxyethylamino-6-nitro phenol,
2-methyl-5-N-methylamino-6-nitro phenol,
2-chloro-5-amino-6-nitro phenol,
2-methyl-5-acetylamino-6-nitro phenol,
2-methyl-5-carbethoxyamino-6-nitro phenol, and
2-methyl-5-N-piperidinoethylamino-6-nitro phenol.

In addition to the couplers of formula (I), there can also be used a further coupler compound. Representative of these further couplers are metadiphenols; metaaminophenols or their derivatives and principally compounds having the formula:

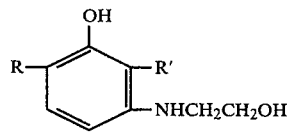

wherein R is selected from the group consisting of hydrogen, alkyl and halogen and R' is selected from the group consisting of hydrogen and alkyl, wherein the alkyl moieties have 1–4 carbon atoms; metadiamines; heterocyclic coupler; and diketonic compounds.

Representative of these further couplers are the following compounds:
6-hydroxy phenomorpholine,
3-N-β-hydroxyethylamino phenol,
6-amino phenomorpholine,
2-methyl-5-N-β-hydroxyethylamino phenol,
resorcinol,
2,6-dimethyl-3-amino phenol,
2-methoxy-5-N,β-hydroxyethylamino phenol,
2,4-diamino anisole dihydrochloride, and
2-methyl-5-acetylamino phenol.

Representative oxidation bases of formula (II) exhibiting the greatest interest relative to the present invention are the following compounds:
2-methyl-4-amino-N-mesylamino ethyl aniline, sulfate
3-methoxy-4-amino-N,N-dimethyl aniline sulfate,
2,6-dimethyl-4-amino phenol,
4-amino-N-acetylamino ethylaniline sulfate,
3-methyl-4-amino-N,N-ethyl, carbamylmethylaniline,
3-methyl-4-amino-N,N-ethyl, mesylaminoethylaniline,
N-methylparaphenylenediamine dihydrochloride,
paratolylenediamine dihydrochloride,
para-amino phenol,
2,6-dimethyl-3-methoxy paraphenylene diamine dihydrochloride,
2-methyl-5-methoxy paraphenylenediamine dihydrochloride,
2-methoxy-4-amino-N,β-hydroxyethylaniline sulfate,
4-amino-N-mesylaminoethylaniline sulfate,
2,5-dimethyl-4-amino phenol,
methoxy paraphenylenediamine dihydrochloride,
paraphenylenediamine,
4-amino-N,N-ethyl, carbamylmethyl aniline,
4-amino-N,N-di-β-hydroxyethylaniline sulfate,
N,N-dimethyl paraphenylenediamine dihydrochloride,
chloroparaphenylenediamine,
3-methyl-4-amino-N-methylaniline dihydrochloride,
3-methoxy-4-amino-N-methylaniline dihydrochloride,
4-amino-N,β-hydroxyethylaniline sulfate,
2-chloro-4-amino-N-methylaniline sulfate,
2-methyl-4-amino-N-methylaniline sulfate,
2-methoxy-4-amino-N-carbamylmethylaniline,
4-amino-N,N-ethyl, β-piperidinoethylaniline trihydrochloride,
4-amino-N,N-ethyl, β-sulfoethylaniline,
3-methoxy-4-amino-N,β-hydroxyethylaniline sulfate,
2-chloro-4-amino-N, acetylaminoethylaniline sulfate,
2-methyl-4-amino-N,β-hydroxyethylaniline sulfate,
3-methyl-4-amino-N,N-ethyl, β-sulfoethylaniline,
3-methyl-4-amino phenol hydrobromide,
2,5-diamino pyridine dihydrochloride,
2,4-dihydroxy-5,6-diamino pyrimidine,
2-chloro-5-N-β-hydroxyethylamino phenol,
2,6-dimethyl-3-N-β-hydroxyethylamino phenol,
m-aminophenol,
2-methyl-5 ureidophenol, and
3-amino-4-methoxy phenol.

In addition to the oxidation bases of formula (II), another oxidation base can also be employed. Representative of said other oxidation bases are heterocyclic bases such as 2,5-diamino pyridine and 2-hydroxy-5-amino pyridine.

Representative other direct dyes usefully employed in the compositions of the present invention include the following:
(4-nitro-5-N-methylamino) phenyl carboxymethylether,
3-nitro-4-N'-methylamino-N,N-methyl, β-hydroxyethylaniline,
tetraamino anthraquinone,
nitro-meta phenylenediamine,
3-methoxy-4,6-diamino-4'-hydroxy diphenylamine trihydrochloride, and
N-[(4'-amino)phenyl]-2-methyl-5-amino benzoquinoneimine.

The dye compositions of the present invention containing in combination at least one nitrated compound of formula (I) and at least one oxidation base of formula (II) provide strong and very stable colorations which exhibit remarkable stability to light, to weather and to washing. When the oxidation base employed is a para-aminophenol of formula (II) wherein Y is hydroxyl, an indophenol which provides coppery shades, which are more or less orange pink, is produced.

When as the oxidation base there is employed a paraphenylenediamine of formula (II) wherein Y is —NR₅R₆, an indamine providing strong green, blue and violet colorations is produced. In particular, those paraphenylenediamines carrying a methoxy group on the ring provide, on condensation with the couplers of formula (I), very strong blue colorations having good stability to light and to weather, as shown in Examples T22, T37, T48 and T51.

The compounds of formula (I) provide then, by oxidative condensation with para-aminophenols as well as with paraphenylenediamines, shades which are equally stable to light and to weather. This is not the case, for example, with other couplers such as 2,4-diamino anisole which give with para amino phenol an orange coloration unstable to light.

It has also been known that meta-diamines produce, as do the nitro meta-amino phenols of the present invention, a range of blue colorations when used with para phenylene damines, although when heretofore known meta-diamines are employed with the para aminophenols, yellow colors which are unstable to light are produced. On the other hand, the nitrated couplers of the present invention provide extremely stable colorations, by coupling not only with para phenylene diamines but also with para amino phenols.

Thus, in accordance with the present invention, there can be included in a single dye composition the coupler of formula (I) and both a para amino phenol and a para phenylene diamine, of formula (II). According to the choice of the para phenylenediamine, there is obtained either a range of chestnut and beige colors having good stability to light, as evidenced in Examples T25, T27, T43, T31 and T57, or a range of greys also having a good stability to light, the dark grey shades being preferably obtained with a para phenylenediamine carrying a methoxy group on the ring, as shown in Examples T44, T52, T56 and T14.

Finally, the dye composition of the present invention can contain a sufficient excess of compound (I) in the presence of one or more oxidation bases of formula (II) so as to provide, because of the good stability of the compound of formula (I), in the presence of oxidizing and alkalinizing agents, and also because of its good coloring characteristics, the attainment in a very reproducible manner the coloration obtained in situ by the nitro-indophenols, or the nitro-indoanilines resulting from a previous oxidative condensation with oxidation bases.

The couplers of the present invention exhibit high coupling speed even, vis-a-vis, those bases with which the coupling is generally effected in a slow fashion.

The dye composition of the invention contains a coupler component, which is principally the coupler of formula (I), in a total amount of 0.002 to 2 weight percent, and an oxidation base which is principally the oxidation base of formula (II) in a total amount of 0 to 2 weight percent, based on the total weight of said dye composition. Further, the composition of the present invention has a pH which can vary from 5 to 11. The molar ratio of coupler:oxidation base can vary from 1:5 to 5:1, in those instances when an oxidation base is included in the said composition. However, particularly interesting compositions are those wherein the ratio of coupler:oxidation base is greater than 1, since in these compositions the coupler also functions as a direct dye.

The dye compositions of the present invention can be provided in the form of non-ionic, amphoteric, cationic or anionic compositions.

Further, the compositions of the present invention can also be employed with an aqueous or hydroalcoholic carrier, where, in the latter, the alcohol component is a lower alkanol, preferably ethanol or isopropanol, or even another alcohol type solvent such as a glycol, for instance, butyl glycol, the monoethyl ester of diethylene glycol and the like, in an amount ranging up to about 40 weight percent of said composition, preferably about 1 to 40 weight percent.

The composition of the present invention can also contain a cationic, anionic or amphoteric surface active agent in an amount ranging up to 20 weight percent. Representative surface active agents include fatty alcohol sulfates, fatty acid ethanolamides, polyoxyethylenated fatty acids and alcohols, thickening agents such as carboxymethyl cellulose, and higher fatty alcohols. The compositions of the present invention can contain as a carrier in an aqueous medium, principally the following products or mixtures: carboxymethyl cellulose-ethyl alcohol; alkaline lauryl sulfate-oxyethylenated alcohol-ethylenediamine tetra-acetic acid; lauryl alcohol; alkaline alkylsulfates-Carbopol 934-butyl glycol; lauryl alcohol-butyl glycol; propylene glycol-nonylphenol; diethanolamide of the fatty acids of copra-propylene glycol; nonylphenolbutyl glycol; diethanolamide of the fatty acids of copraethanol; oleyl alcohol-propylene glycol; Carbopol 934-ethanol; nonylphenol-ethanol; oleyl alcohol-butyl glycol; nonylphenolethyl glycol; carboxymethyl cellulose-propylene glycol; and lauryl alcohol-butyl glycol.

The composition of the present invention can also contain an oxidizing agent such as $H_2O_2$, potassium ferricyanide or a persalt such as ammonium persulfate.

Moreover, the composition of the present invention can contain perfumes; antioxidant agents; sequesterants; an alkalinizing agent such as ammonia, sodium phosphate, sodium carbonate or an alkanol amine; or an acidifying agent such as phosphoric acid, lactic acid, acetic acid and the like.

The present invention also relates to a process for dyeing keratinic fibers, especially living human hair, employing the compounds of formula (I) either as a direct dye or as a coupler in the presence of an oxidation base.

When the compound of formula (I) is used as a direct dye, the composition is directly applied to the keratinic fibers and the composition is permitted to remain in contact therewith for a period of time ranging from about 10 to 30 minutes. Thereafter the fibers are rinsed, shampooed and then dried.

However, it is in the use of the compounds of formula (I) of the present invention in an oxidation dyeing operation that is of the greatest interest. According to a first embodiment, there is initially prepared a cosmetic composition for application to the hair containing both the coupler of formula (I) and an oxidation base, preferably an oxidation base of formula (II). At the moment of use, there is added thereto a cosmetic oxidizing agent, i.e. $H_2O_2$, a ferricyanide or a persalt and the resulting mixture is then thoroughly homogenized with the resulting homogeneous mixture then being applied to the keratinic fibers, the said mixture being permitted to remain in contact with the said fibers for a period of time ranging from about 10 to 30 minutes. Thereafter the fibers are rinsed, shampooed and then dried.

With the couplers of formula (III):

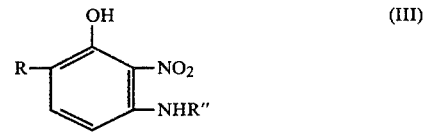

in which R has the aformentioned values and R″ is hydrogen, alkyl, hydroxy alkyl, carbamylalkyl, mesylaminoalkyl, aminoalkyl, acylaminoalkyl, monoalkylaminoalkyl, dialkylaminoalkyl, piperidinoalkyl or morpholinoalkyl, any cosmetic oxidizing agent can be employed with comparable results. The alkyl moiety of R″ in formula (III) contains 1-4 carbon atoms.

However, with compounds of formula (IV):

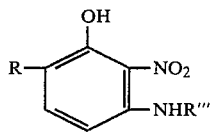

(IV)

wherein R has the aforementioned values and R‴ is carbamoyl, acyl, or carbalkoxy, wherein the alkoxy moiety has 1-4 carbon atoms, better results are obtained by using as the oxidizing agent a persalt, preferably, ammonium persulfate.

Because of the rapidity with which the compounds of formula (I) couple with an oxidation base, an important embodiment of the present invention comprises carrying out the dyeing in situ, principally in the case of dyeing living human hair, thereby providing some particularly desirable effects and notably the attainment of variations in the color produced. To this end, there can initially be applied to the hair either a solution containing the coupler of the present invention and then a solution containing an oxidation base, the oxidizing agent being contained in one or the other of said solutions; initially there can be applied to the hair a solution containing an oxidation base and then a solution containing the coupler of the present invention, the oxidizing agent being contained in one or the other of said solutions. In either instance, the solutions are permitted to remain in contact with the hair for a period of time ranging from about 10 to 30 minutes.

The present invention then further relates to:
(a) the compounds of formula (I);
(b) a process for preparing the compounds of formula (I);
(c) indo compounds resulting from the coupling of a coupler of formula (I) and an oxidation base, particularly an oxidation base of formula (II);
(d) a process for the preparation of said indo compounds of (c);
(e) a composition containing said indo compounds of (c); and
(f) a process for using the composition containing said indo compounds of (c).

The novel compounds of formula (I) are those for which R and R′ have the values stated above with the proviso that R and R″ are not, simultaneously, hydrogen.

The compounds of formula (I) can be prepared, either by nitration of corresponding meta-amino phenols, or by substitution on the nitrogen atom of the amino group of a nitrated meta-amino phenol of formula (I) in which R′ is hydrogen.

In accordance with a first embodiment, the process comprises (a) nitrating with the use of nitric acid in the presence of sulfuric acid in mixture or not with phosphoric acid or acetic anhydride or ethyl phosphate, at a low temperature with agitation, a compound having the formula (V):

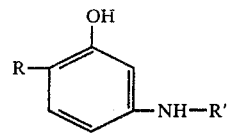

(V)

wherein R is alkyl or halogen and R′ is acyl, preferably acetyl, so as to provide a mixture of isomers nitrated on the ortho and para positions relative to the phenol function, as well as a small amount of a derivative dinitrated at the ortho and para positions;

(b) separating from the reaction mixture the derivative nitrated in the ortho position;

(c) treating the thus separated ortho nitrated derivative with HCl to liberate the primary amine function; and (d) optionally effecting mono-substitution of the primary amine group, by a radical R′ such as defined in formula (I) above, said R′ being other than hydrogen.

In this first embodiment, the addition of acetic anhydride, phosphoric acid or ethyl phosphate, avoids mass solidification, by crystallization, due to the use of sulfuric acid.

While the operation of the second embodiment is well known, the attainment of a substitution, only on the amino group, while leaving intact the phenol function, was completely unexpected.

According to this second embodiment, the process comprises (a) mono-substituting the —NH₂ group on a compound of the formula

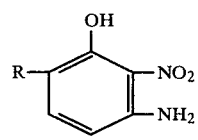

(VI)

in which R is lower alkyl having 1-4 carbon atoms or halogen, with a radical R′ having the value defined for the compound of formula (I) but different from hydrogen, in an aqueous alkaline medium or in a water-organic solvent medium, at a temperature between 25° C. and the reflux of the solvent or mixture of solvents;

(b) permitting the reaction mixture to stand at ambient temperature; and (c) separating from the reaction mixture the desired product which has precipitated by cooling or by the addition thereto of a solvent.

The implementation of this second embodiment provides principally chromatographically pure 2-methyl-5-methylamino-6-nitro phenol.

A third embodiment permits to obtain with a higher degree of purity, compounds of formula (I) wherein R′ is acetyl, R being lower alkyl containing 1-4 carbon atoms or halogen. In accordance with this embodiment, the process comprises (a) reacting a compound of formula (VI) wherein R has the values given above with a mixture of acetic anhydride-sulfuric acid, with agitation;

(b) adjusting the temperature of the reaction mixture to ambient temperature, eliminating excess acetic anhydride by the addition of ice water and separating therefrom the corresponding diacetylated product;

(c) deacetylating the phenol function with an alkaline solution; and (d) precipitating the desired product, with a sufficient amount of acetic acid. Optionally, the precipitated product after separation from the reaction mixture can be recrystallized.

The implementation of this third embodiment produces advantageously, 2-methyl-5-acetylamino-6-nitro phenol in a pure state.

From the fact that the compounds of formula (I), wherein R and R' are not simultaneously hydrogen, are new compounds, it results from it that the compounds obtained by condensation with oxidation bases and principally with oxidation bases of formula (II) are also new compounds which are besides contained in the oxidation dye compositions of the present invention. This condensation is carried out either before the use of the dye composition, or in situ by successive application of a solution containing the compound of formula (I) and a solution containing an oxidation base, on keratinic fibers.

These new compounds comrise indo-nitro anilines or indo-nitrophenols having the formula

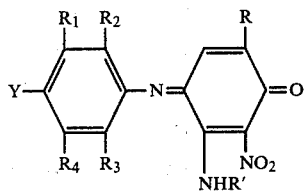

wherein R, R', $R_1$, $R_2$, $R_3$, $R_4$, $R_5$, $R_6$ and Y have the values mentioned for the compounds of formula (I).

These nitrated indophenols and nitrated indamines provide strong colors which are very stable and exhibit remarkable stability to light, to weather and to washing.

Representative compounds of formula (VII) include the following benzoquinoneimines:

N-[(4'-hydroxy)phenyl]-2-methyl-5-amino-6-nitro benzoquinoneimine,

N-[(4'-hydroxy-2'-chloro)phenyl]-2-methyl-5-amino-6-nitro benzoquinoneimine,

N-[(4'-amino-2'-methoxy-5'-methyl)phenyl]-2-methyl-5-amino-6-nitro benzoquinoneimine, N-[(4'-amino-2',5'-dimethyl)phenyl]-2-methyl-5-amino-6-nitro benzoquinoneimine, N-[(4'-amino-2',5'-dimethyl)phenyl]-2-methyl-5-acetylamino-6-nitro benzoquinone imine, N-[(4'-amino-3'-chloro)phenyl]-2-methyl-5-amino-6-nitro benzoquinoneimine, N-[(4'-amino-2',5'-dimethyl)phenyl]-2-methyl-5-carbethoxyamino-6-nitro-benzoquinoneimine, N-[(4'-methylamino-3'-chloro)phenyl-2-methyl-5-amino-6-nitro benzoquinoneimine, N-[(4'-β-hydroxyethylamino-3'-methoxy)phenyl]-2-methyl-5-amino-6-nitro benzoquinoneimine, N-[(4'-dimethylamino-2',6'-dimethyl)phenyl]-2-methyl-5-amino-6-nitro benzoquinoneimine, N-[4'-(ethylcarbamylmethyl)amino phenyl]-2-methyl-5-amino-6-nitro benzoquinoneimine and N-[(4'-ethyl,β-morpholinoethylamino-2'-methyl)-phenyl]-2-chloro-5-amino-6-nitro benzoquinoneimine.

The compounds of formula (VII) can be prepared in accordance with a first process wherein a nitrated metaaminophenol of formula (I) wherein R and R' have the values given above is reacted in an alkaline medium with a compound of formula (II) wherein $R_1$, $R_2$, $R_3$, $R_4$ and Y have the values given above. An oxidizing agent is added thereto with agitation. Optionally, the reaction mixture is cooled after which the reaction mixture is left to rest at ambient temperature to obtain by precipitation the compound of formula (VII).

In accordance with a second process, a compound of formula (I) wherein R and R' have the values given above is reacted in an alkaline medium with a compound of formula (VIII)

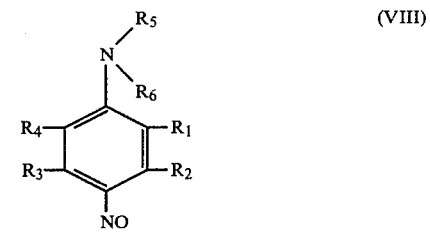

wherein $R_1$, $R_2$, $R_3$, $R_4$, $R_5$ and $R_6$ have the values given above. The desired product is obtained by precipitation which occurs when the above reaction mixture is permitted to stand at ambient temperature.

These two processes can be carried out in an aqueous, hydroalcoholic or hydroacetonic medium, which is generally ammoniacal. In the first process, there can be employed as the oxidizing agent, $H_2O_2$, potassium ferricyanide or a persalt such as ammonium persulfate.

The nitro-indophenols and the nitro-indoanilines formed by the condensation at the interior of the keratinic fiber, as well as at the exterior thereof when an oxidation dye composition is employed, can be prepared separately and isolated. In this form, the dye is employed as a direct dye and can be incorporated into a dyeing and hair setting lotion, the dyeing thus occurring only at the exterior of the keratinic fiber.

The dyeing and hair setting lotion according to the present invention, contains at least one compound of formula (VII) in an amount of 0.01 to 2 weight percent, preferably from 0.05 to 1 weight percent, in a hydroalcoholic carrier containing from 10 to 70 and preferably from 20 to 50 weight percent alcohol, in the presence of a cosmetic film forming polymer present in an amount ranging from 0.5 to 4, and preferably from 1 to 3, weight percent. The pH of the dyeing and hair-setting lotion composition can range from 4 to 10.5 and preferably from 5.5 to 10. The hydroalcoholic solution contains a low molecular weight alkanol such as, preferably, ethanol or isopropanol.

Representative cosmetic resins usefully employed in the dyeing and hair-setting lotion composition of the present invention include the following for which there is indicated a chemical name, optionally a commercial name, and if necessary a phyico-chemical characteristic:

PVP K30—Polyvinylpyrrolidone (MW-40,000);
PVP K60—Polyvinylpyrrolidone (MW-160,000);
PVP K90—Polyvinylpyrrolidone (MW-360,000);
(PVP/VA) E735—Polyvinylpyrrolidone/vinyl acetate, 70/30, MW-40,000;
(PVP/VA) E535—Polyvinylpyrrolidone/vinyl acetate, 50/50;
(PVP/VA) E335—Polyvinylpyrrolidone/vinyl acetate, 30/70, MW-160,000;
(PVP/VA) S630—Polyvinylpyrrolidone/vinyl acetate, 60/40, viscosity determined at 25° C. for a 5% solution in ethanol—3.3 to 4 cps, as well as the following resins for which one indicates the specific viscosity (cps) measured for a 1% solution in methylethyl ketone at a temperature of 25° C.;
methylvinylether/maleic anhydride, 50:50, known under the mark "Gantrez AN 119", viscosity—0.-1-0.5;
"Gantrez AN 139" viscosity—1.0-1.4;
"Gantrez 149" viscosity—1.5-2;
"Gantrez AN 169" viscosity 2.6-3.5;
"Gantrez ES 225", the monoethyl ester of Gantrez AN 119;
"Gantrez ES 335-1", the isopropyl monoester of "Gantrez AN 119";
"Gantrez ES 425", the butyl monoester of "Gantrez AN 119";
"Gantrez ES 435", the butyl monoester of "Gantrez AN 119";
crotonic acid/vinyl acetate, 10:90, MW—50,000;
Resine 28-13-10, copolymer of vinyl acetate/crotonic acid, MW—20,000;
terpolymer of carboxylated vinyl acetate (intrinsic viscosity—0.32 in acetone at 30° C.);
terpolymer of vinyl acetate, allyl stearate and allyloxy acetic acid (80:15:5)—4.4 to 5 cps in a 5% solution in dimethyl formamide at 35° C.,
"Gafquat 734"-quaternary copolymer of polyvinylpyrrolidone in a 50% solution of ethyl alcohol, MW—100,000;
and
a terpolymer of methyl methacrylate, stearyl methacrylate and dimethyl amino ethyl methacrylate, completely quaternized with dimethyl sulfate (20.15:22.35:57.50% by weight), intrinsic viscosity of 8-12 cps in a 5% solution in dimethylformamide at 35° C.

The dyeing and hair-setting lotions of the present invention can also contain other direct dyes such as anthraquinone dyes, nitrobenzene dyes, as well as indamines, indophenols and indoanilines having a formula different from the indo compounds of formula (VII).

These lotions can be applied on any type of keratinic fiber, they are employed preferably on naturally white or previously bleached living human hair. The application is carried out on hair still moist after washing and rinsing, the hair then being rolled up so as to set it and then dried in a conventional manner.

The following non-limiting examples in which the temperatures are indicated in degrees centigrade, have for their end to illustrate the various aspects of the present invention. Unless otherwise indicated, all parts and percentages are by weight.

SUMMARY TABLE OF COMPOUNDS OF FORMULA (I)

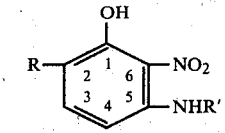

PREPARED IN EXAMPLES I TO VII

| Example No* (1) | Compound of Formula (I) (2) | Empirical Formula (3) | Melting Point (°C.) (4) | R (5) | R' (6) |
|---|---|---|---|---|---|
| I | 2-methyl-5-amino-6 nitro-phenol | $C_7H_8N_2O_3$ | 130 | $CH_3$ | H |
| II | 2-methyl-5-N-B-hydroxyethylamino-6 nitro-phenol | $C_9H_{12}O_4N_2$ | 103 | $CH_3$ | $CH_2CH_2OH$ |
| III | 2-methyl-5-N-methylamino-6 nitro-phenol | $C_8H_{10}N_2O_3$ | 140 | $CH_3$ | $CH_3$ |
| IV | 2-chloro-5 amino-6 nitro-phenol | $C_6H_5N_2O_3Cl$ | 184 | Cl | H |
| V | 2-methyl-5 acetylamino-6 nitro-phenol | $C_9H_{10}N_2O_4$ | 147 | $CH_3$ | $COCH_3$ |
| VI | 2-methyl-5 carbethoxyamino-6 nitro-phenol | $C_{10}H_{12}N_2O_5$ | 115 | $CH_3$ | $COOC_2H_5$ |
| VII | 2-methyl-5-N-piperidinoethylamino-6 nitro-phenol | $C_{14}H_{21}O_3N_3$ | 82 | $CH_3$ | $CH_2-CH_2-$ piperidino |

EXAMPLES OF PROCESS FOR THE PREPARATION OF COMPOUNDS OF FORMULA (I)

EXAMPLE NO. I

Preparation of 2-methyl-5-amino-6-nitro phenol in accordance with the following reaction scheme:

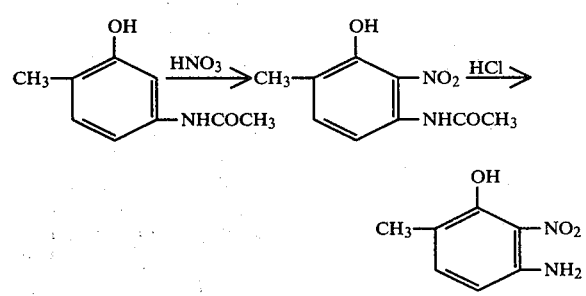

1st phase

Preparation of 2-methyl-5-acetylamino-6-nitro phenol.

0.606 mole (100 g) of 2-methyl-5-acetylamino phenol is dissolved, with agitation, in 900 cc of sulfuric acid (d=1.83) at a temperature close to 0° C. 20 cc of phosphoric acid are then added and the mixture is cooled to −30° C. Thereafter, there are slowly added, with good agitation, while maintaining the temperature between −33° and −30° C., 25 cc of nitric acid (d=1.52) in 400 cc of sulfuric acid (d=1.83) over a period of about one hour. The sulfonitric mixture is then poured onto 8 kgs of shaved ice.

The resulting nitrated derivative is then filtered, washed with water and dried, yielding 94 g of the crude nitrated product which contains a little 2-methyl-4-nitro-5-acetylamino phenol.

2nd phase

Preparation of 2-methyl-5-amino-nitro-6-phenol 92 g of the crude nitrated derivative obtained in the 1st phase are dissolved in 200 cc of HCl (d=1.19) to which have been added 200 cc of acetic acid. The resulting mixture is heated to reflux for 1½ hours. Thereafter the reaction medium is cooled to a temperature of about −15° C. whereby 2-methyl-5-amino-6-nitro phenol hydrochloride precipitates. This precipitate is then filtered, washed with 50 cc of a 50:50 mixture of HCl-acetic acid at −10° C., and treated with 400 cc of water with agitation for a few minutes to yield 2-methyl-5-amino-nitro-6-phenol which is then filtered and crystallized in ethanol, yielding 45 g of chromatographically pure product having a melting point of 130° C.

| Elemental analysis: C₇H₈N₂O₃ | | |
|---|---|---|
| | Calculated | Theory |
| C % | 50.00 | 50.05 |
| H % | 4.76 | 4.99 |
| N % | 16.67 | 16.57 |

Variation of the 1st phase:

Preparation of 2-methyl-5-acetylamino-6-nitro phenol 0.3 mole (49.5 g) of 2-methyl-5-acetylamino phenol partially in solution is added with agitation to a mixture of 120 cc of acetic anhydride and 580 cc of sulfuric acid (d=1.83), the temperature being maintained between −5° C. and +5° C. The resulting reaction medium is cooled to −30° C. after which there are slowly added with very good agitation, while maintaining the temperature between −33° C. and −30° C., 12.5 cc of nitric acid (d=1.52) in 18 cc of sulfuric acid. This addition lasts about 30 minutes.

The reaction mixture is then poured over 3 kg of crushed ice and the resulting precipitated nitrated derivative is filtered, washed with water and dried, yielding 45 g of crude nitrated derivative which contains a little 2-methyl-4-nitro-5-acetylamino phenol. 2nd phase: unchanged.

EXAMPLE NO. II

Preparation of 2-methyl-5-N-β-hydroxyethyl amino-6-nitro phenol according to the following reaction scheme:

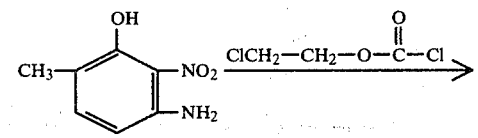

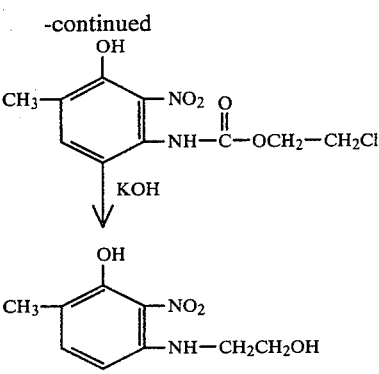

1st phase

Preparation of N-[(2-nitro-3-hydroxy-4-methyl)phenyl] β-chloroethyl carbamate 0.05 mole (8.4 g) of 2-methyl-5-amino-6-nitro phenol is dissolved in 30 cc of dioxan. Thereafter 0.0365 mole (3.65 g) of calcium carbonate is added to the solution and the resulting mixture is heated to a temperature of about 70° C., after which, little by little, while agitating, 0.073 mole (10.47 g) of β-chloroethyl chloroformate is added thereto. The agitation is maintained for 50 minutes at about 70° C. at which point the warm reaction mixture is filtered. After cooling and diluting the filtrate with water, 12.5 g of N-[(2-nitro-3-hydroxy-4-methyl)-phenyl] β-chloroethyl carbamate precipitate and are separated by filtration. This product melts at 82° C.

2nd phase

Preparation of 2-methyl-5-N-β-hydroxyethylamino-6-nitro phenol.

0.0182 mole (5 g) of N-[(2-nitro-3-hydroxy-4-methyl)-phenyl] β-chloroethyl carbamate is dissolved in 15 cc of a 5 N potassium hydroxide solution. The solution is heated for 30 minutes at 60° C. after which 15 cc of water are added and the resulting mixture is cooled to 0° C. There are then added 15 cc of 0.5 N HCl and the expected product in the form of a crystalline precipitate is separated by filtration. After recrystallization in ethyl acetate and drying under a vacuum, the product obtained melts at 103° C.

| Elemental analysis: C₉H₁₂O₄N₂ | | |
|---|---|---|
| | Calculated | Found |
| C% | 50.94 | 50.63 |
| H% | 5.66 | 5.71 |
| N% | 13.21 | 13.39 |

EXAMPLE NO. III

Preparation of 2-methyl-5-N-methylamino-6-nitro phenol

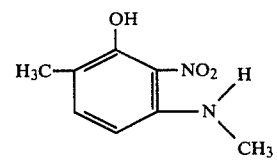

0.02 mole (3.36 g) of 2-methyl-5-amino-6-nitro phenol is dissolved in 22 cc of a normal sodium hydroxide solution at a temperature of about 40° C. There is then added 0.022 mole (2.77 g) of methyl sulfate and the reaction mixture is maintained at 40° C. for two hours. 22 cc of a normal NaOH solution and 0.022 mole of methyl sulfate are added and the resulting reaction mixture is left to rest overnight at ambient temperature. The next day the expected product which has precipitated in the form of a thick oil is decanted. This oil, washed with water to which are added 5 cc of acetone, soon crystallizes and the crystals are separated by filtration. The recovered crystals are completely soluble in a normal NaOH solution and are chromatographically pure. They do not contain any initial reactant and after recrystallization in a benzene-hexane mixture and drying under a vacuum, the said product exhibits a melting point of 140° C.

| Elemental analysis: $C_8H_{10}N_2O_3$ | | |
|---|---|---|
| | Calculated | Theory |
| C% | 52.84 | 53.03 |
| H% | 5.53 | 5.46 |
| N% | 15.38 | 15.50 |

EXAMPLE NO. IV

Preparation of 2-chloro-5-amino-6-nitro phenol according to the following reaction scheme:

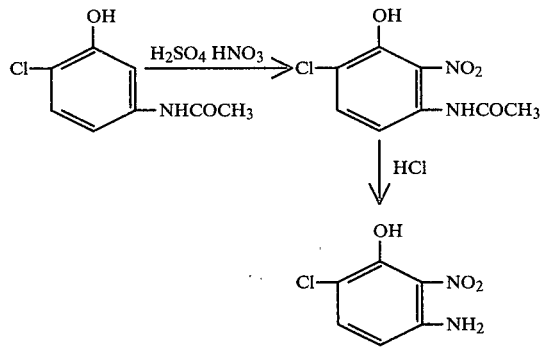

1st phase
Preparation of 2-chloro-5-acetylamino-6-nitro phenol 0.23 mole (43 g) of 2-chloro-5-acetylamino phenol is dissolved, with agitation, in 500 cc of sulfuric acid (d=1.83) at a temperature of about +5° C. There are then added 15 cc of phosphoric acid and the resulting reaction medium is cooled to −30° C. There are then slowly added, over a 35 minute period, while vigorously agitating, 9.7 cc of nitric acid (d=1.52) in 1.5 cc of sulfuric acid (d=1.83). The reaction mixture is then poured over 3 kgs of shaved ice to precipitate the desired product which is separated by filtration, washed with water and dried, yielding 47 g of product.

2nd phase
Preparation of 2-chloro-5-amino-6 -nitro phenol

The crude nitrated product (47 g) obtained above is introduced into 235 cc of HCl (d=1.19) to which have been added 180 cc of acetic acid. The resulting mixture is heated to reflux for 1½ hours to obtain the complete solution of the product.

The reaction mixture is then cooled to −5° C. to precipitate 2-chloro-5-amino-6-nitro phenol hydrochloride, which is then separated by filtration, washed with 50 cc of a mixture of HCl and acetic acid at 0° C. and then treated with 200 cc of water while agitating the whole for a few minutes to liberate the 2-chloro-5-amino-6-nitro phenol. This product is then separated by filtration and recrystallized in ethanol, yielding 28 g of chromatographically pure product melting at 184° C.

| Elemental analysis: $C_6H_5N_2O_3Cl$ | | |
|---|---|---|
| | Calculated | Theory |
| C% | 38.20 | 38.03 |
| H% | 2.65 | 2.65 |
| N% | 14.85 | 14.75 |
| Cl% | 18.83 | 18.97, 18.82 |

EXAMPLE NO. V

Preparation of 2-methyl-5-acetylamino-6-nitro phenol in the pure state

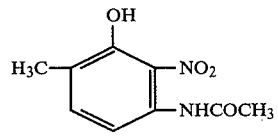

1st phase
Preparation of 2-methyl-5-acetylamino-6-nitro acetyl phenol

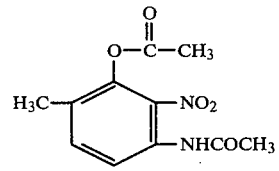

0.002 mole (3.36 g) of 2-methyl-5-amino-6-nitro phenol is dissolved in 15 cc of acetic anhydride. There are then added 2 drops of concentrated sulfuric acid and the reaction mixture is agitated for 2 hours. The temperature of the reaction mixture is then raised to 45° C. and subsequently reduced progressively to ambient temperature, at which point the solution is poured over 50 g of ice water. When the acetic anhydride is destroyed, the diacetylated product which has precipitated in the form of crystals is filtered, washed with ice water and dried. The said product has a melting point of 172° C.

2nd phase
Preparation of 2-methyl-5-acetylamino-6-nitro phenol.

0.0119 mole (3 g) of the diacetylated product obtained above is added to 55 cc of a 0.4 N NaOH solution. The product dissolves very rapidly, the deacetylation of the phenol function being nearly immediate.

To the NaOH solution there is added a sufficient amount of acetic acid to re-precipitate the 2-methyl-5-acetylamino-6-nitro phenol which is then separated by filtration, washed with water, recrystallized in ethyl alcohol (95° titer) and dried under a vacuum. The product has a melting point of 147° C.

| Elemental analysis: $C_9H_{10}N_2O_4$ | | |
|---|---|---|
| | Calculated | Theory |
| C% | 51.43 | 51.35 |
| H% | 4.76 | 4.78 |
| N% | 13.33 | 13.50 |

EXAMPLE NO. VI

Preparation of 2-methyl-5-carbethoxyamino-6-nitro phenol

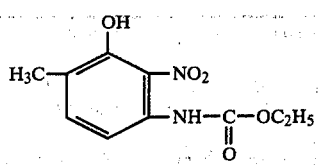

0.1 mole (16.8 g) of 2-methyl-5-amino-6-nitro phenol is introduced into 30 cc of dioxan. To this mixture there is added 0.055 mole (5.5 g) of calcium carbonate. The resulting mixture is heated to reflux, while agitating, and to it there is added little by little, 0.11 mole (11.93 g) of ethyl chloroformate. Reflux is maintained for 1 hour, after which the boiling mixture is filtered to remove the mineral salts. After cooling the filtrate, the 2-methyl-5-carbethoxyamino-6-nitro phenol crystallizes and is then recrystallized in ethanol, separated and dried under a vacuum. This product has a melting point of 115° C.

| Elemental analysis: $C_{10}H_{12}N_2O_5$ | | |
|---|---|---|
| | Calculated | Found |
| C% | 50.00 | 49.97 |
| H% | 5.04 | 4.70 |
| N% | 11.66 | 11.61 |

EXAMPLE NO. VII

Preparation of 2-methyl-5-N-piperidinoethylamino-6-nitro phenol according to the following reaction scheme:

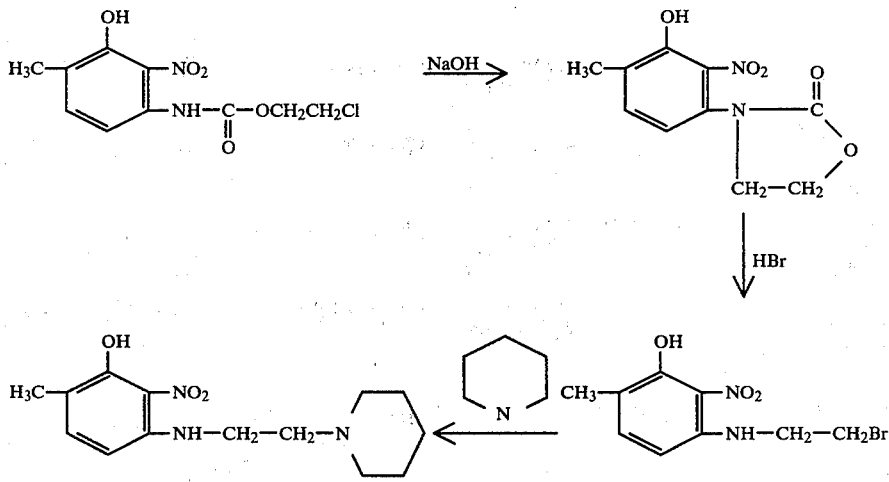

1st phase

Preparation of N-[(2'-nitro-3'-hydroxy-4'-methyl)-phenyl]-1,3-oxazolidine-2-one 0.0364 mole (10 g) of N-[(2'-nitro-3'-hydroxy-4'-methyl)phenyl]-$\beta$-chloroethyl carbamate (obtained in the 1st phase of Example No. II) is introduced into 728 cc of a normal NaOH solution (0.0728 mole) cooled to about 0° C. The resulting mixture is stirred for 25 minutes while the temperature thereof is maintained at about 10° C. There is then added acetic acid in an amount sufficient to precipitate the expected product, which is filtered, washed with water, recrystallized in acetic acid and dried under a vacuum, yielding a product which melts at 153° C.

| Elemental analysis: $C_{10}H_{10}N_2O_5$ | | |
|---|---|---|
| | Calculated | Found |
| C % | 50.42 | 50.34 |
| H % | 4.20 | 4.50 |
| N % | 11.76 | 11.79 |

2nd phase

Preparation of 2-methyl-5-N-$\beta$-bromoethylamino-6-nitro phenol.

0.0252 mole (6 g) of N-[(2'-nitro-3'-hydroxy-4'-methyl)phenyl]-1,3 oxazolidin-2-one is introduced into 30 cc of 66% HBr. The resulting mixture is heated for 1½ hours over a boiling water bath. Thereafter the reaction mixture is poured into 90 cc of ice water.

The desired product which precipitates, is filtered, washed with water, recrystallized in acetic acid and dried under a vacuum. This product melts at 129° C.

| Elemental analysis: $C_9H_{11}O_3N_2Br$ | | |
|---|---|---|
| | Calculated | Theory |
| C % | 39.27 | 39.15 |
| H % | 4.00 | 4.30 |
| N % | 10.18 | 10.12 |
| Br % | 29.09 | 29.22 |

3rd phase

Preparation of 2-methyl-5-N-piperidinoethylamino-6-nitro phenol 0.0073 mole of 2-methyl-5-N-$\beta$-bromoethylamino-6-nitro phenol is introduced into 10 cc of piperidine. The resulting mixture is heated for 15 minutes at 110° C., after which the solution is cooled to ambient temperature and then poured into 15 cc of water. After the addition of acetic acid, the desired product which precipitates is filtered, washed with water and dried under a vacuum. The product melts at 82° C.

| Elemental analysis: $C_{14}H_{21}N_3O_3$ | | |
|---|---|---|
| | Calculated | Found |
| C % | 60.22 | 60.36 | 60.22 |
| H % | 7.53 | 7.79 | 7.80 |

-continued

| | | N % | 15.05 | 15.34 | 15.28 |
|---|---|---|---|---|---|
| Elemental analysis: $C_{14}H_{21}N_3O_3$ | | | | | |
| Calculated | Found | | | | |

TABLE B

Table B indicates the characteristics of the "indo" or "benzoquinoneimine" compounds of formula (VII).
The different columns of this Table have the following meanings:
(1)    number of the Example for preparing the compound;
(2)    designation of the compound of formula (VII);
(3)    empirical formula
(4)    melting point of the compound having the empirical formula in (3);
(5)    to (12): values for each of the compounds, of the radicals designated respectively by R, R', $R_1$, $R_2$, $R_3$, $R_4$, Y = $NR_5R_6$ and Y = OH. To facilitate the reading of this table, the value H is not represented for the radicals R, R', $R_1$, $R_2$, $R_3$ and $R_4$;
(13)   to (16): these columns indicate respectively in weight percent the amounts of the elements C, H, N and Cl, corresponding on the one hand (1st line) to the calculated values and on the other hand (2nd line) to the results found by elemental analysis for the compounds whose empirical formula is indicated in column (3).
In Examples XVIII, the analytic determination has been carried out in the following manner:
Molecular mass calculated for $C_{17}H_{19}N_5O_4$: 357
Molecular mass found by potentiometric dosage in acetic acid by perchloric acid: 362.

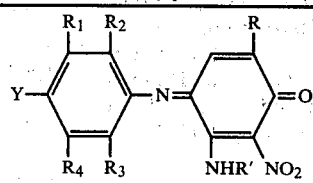

RELATIVE TO COMPOUNDS OF FORMULA VII

| Example No. (1) | Name of the Compound of Formula (VII) (2) | Empirical Formula (3) | Melting Point (°C.) (4) | R (5) | R' (6) | $R_1$ (7) | $R_2$ (8) | $R_3$ (9) | $R_4$ (10) |
|---|---|---|---|---|---|---|---|---|---|
| VIII | N-[(4'-hydroxy)phenyl] 2-methyl-5-amino-6-nitro-benzoquinoneimine | $C_{13}H_{11}N_3O_4$ | 260 with decomposition | $CH_3$ | | | | | |
| IX | N-[(4'-hydroxy-2'-chloro)phenyl]2-methy-5-amino-6-nitro-benzoquinoneimine | $C_{13}H_{10}N_3O_4Cl$ | 260 with decomposition | $CH_3$ | | | Cl | | |
| X | N-[(4'-amino-2'-methoxy-5'-methyl)-phenyl]2-methyl-5-amino-6-nitro-benzoquinoneimine | $C_{15}H_{16}N_4O_4$ | 260 with decompostion | $CH_3$ | | | $OCH_3$ | | $CH_3$ |
| XI | N-[(4'-amino-2',5'-dimethyl)phenyl] 2-methyl-5-amino-6-nitro-benzoquinoneimine | $C_{15}H_{16}N_4O_3 \cdot H_2O$ | 260 with decomposition | $CH_3$ | | | $CH_3$ | | $CH_3$ |
| XII | N-[(4'-amino-2',5'-dimethyl)phenyl]2-methyl-5-acetylamino-6-nitro-benzoquinoneimine | $C_{17}H_{18}N_4O_4$ | 235 decomposition | $CH_3$ | $COCH_3$ | | $CH_3$ | | $CH_3$ |
| XIII | N-[(4'-amino-3'-chloro)phenyl]2-methyl-5-amino-6-nitro-benzoquinoneimine | $C_{13}H_{11}ClN_4O_3$ | 260 with decomposition | $CH_3$ | | | | Cl | |
| XIV | N-[(4'-amino-2',5'-dimethyl)phenyl]2-methyl-5-carbethoxy-amino-6-nitro-benzoquinoneimine | $C_{18}H_{20}N_4O_5$ | 242 with decomposition | $CH_3$ | $CO_2C_2H_5$ | | $CH_3$ | | $CH_3$ |
| XV | N-[(4'-methylamino-3'-chloro)phenyl]2-methyl-5-amino-6-nitro-benzoquinoneimine | $C_{14}H_{13}N_4O_3Cl$ | 246 | $CH_3$ | | | | Cl | |
| XVI | N-[(4'-β-hydroethyl-amino-3'-methoxy)-phenyl]2-methyl-5-amino-6-nitro-benzoquinoneimine | $C_{16}H_{18}N_4O_5$ | 163 | $CH_3$ | | $OCH_3$ | | | |
| XVII | N-[(4'-dimethylamino-2',6'-dimethyl)phenyl]-2-methyl-5-amino-6-nitro-benzoquinoneimine | $C_{17}H_{20}N_4O_3$ | 220 | $CH_3$ | | | $CH_3$ | $CH_3$ | |
| XVIII | N-[(4'-ethylcarbamyl-methyl-amino)phenyl]-2-methyl-5-amino-6-nitro-benzoquinoneimine | $C_{17}H_{19}N_5O_4$ | 140 | $CH_3$ | | | | | |
| XIX | N-[(4'-ethyl, β-morpholinoethyl)amino-2'-methyl)phenyl]2- | $C_{21}H_{26}N_5O_4Cl \cdot 0.5 H_2O$ | 130 | Cl | | | $CH_3$ | | |

TABLE B-continued chloro-5-amino-6-nitro-benzoquinoneimine

| Example No. (1) | Name of the Compound of Formula (VII) (2) | Empirical Formula (3) | Melting Point (°C.) (4) | Y = $\underset{R_6}{\overset{R_5}{\diagdown N \diagup}}$ (11) | Y = (12) | C % (13) | H % (14) | N % (15) | Cl % (16) |
|---|---|---|---|---|---|---|---|---|---|
| VIII | N-[(4'-hydroxy)phenyl]2-methyl-5-amino-6-nitro-benzoquinoneimine | $C_{13}H_{11}N_3O_4$ | 260 with decomposition | | OH | 57.14<br>57.13 | 4.06<br>4.22 | 15.38<br>15.16 | |
| IX | N-[(4'-hydroxy-2'-chloro)phenyl]2-methyl-5-amino-6-nitro-benzoquinoneimine | $C_{13}H_{10}N_3O_4Cl$ | 260 with decomposition | | OH | 50.74<br>50.86 | 3.27<br>3.47 | 13.66<br>13.66 | 11.52<br>11.36 |
| X | N-[(4'-amino-2'-methoxy-5'-methyl)-phenyl]2-methyl-5-amino-6-nitro-benzoquinoneimine | $C_{15}H_{16}N_4O_4$ | 260 with decomposition | $NH_2$ | | 56.96<br>56.57 | 5.10<br>5.04 | 17.71<br>17.48 | |
| XI | N-[(4'-amino-2'-5'-dimethyl)phenyl]2-methyl-5-amino-6-nitro-benzoquinoneimine | $C_{15}H_{16}N_4O_3 \cdot H_2O$ | 260 with decompostion | $NH_2$ | | 56.60<br>57.00 | 5.66<br>5.66 | 17.61<br>17.70 | |
| XII | N-[(4'-amino-2',5'-dimethyl)phenyl]2-methyl-5-acetylamino-6-nitro-benzoquinoneimine | $C_{17}H_{18}N_4O_4$ | 235 decomposition | $NH_2$ | | 59.64<br>59.84 | 5.30<br>5.42 | 16.37<br>16.10 | |
| XIII | N-[(4'-amino-3'-chloro)phenyl]2-methyl-5-amino-6-nitro-benzoquinoneimine | $C_{13}H_{11}ClN_4O_3$ | 260 with decomposition | $NH_2$ | | 50.91<br>50.83 | 3.71<br>3.90 | 18.27<br>18.05 | 11.56<br>11.38 |
| XIV | N-[(4'-amino-2',5'-dimethyl)phenyl]2-methyl-5-carbethoxy-amino-6-nitro-benzoquinoneimine | $C_{18}H_{20}N_4O_5$ | 242 with decomposition | $NH_2$ | | 58.06<br>57.86 | 5.41<br>5.60 | 15.05<br>15.16 | |
| XV | N-[(4'-methylamino-3'-chloro)phenyl]2-methyl-5-amino-6-nitro-benzoquinoneimine | $C_{14}H_{13}N_4O_3Cl$ | 246 | $-N\underset{CH_3}{\overset{H}{\diagup}}$ | | | | | 11.05<br>10.76 |
| XVI | N-[(4'-β-hydroethyl-amino-3'-methoxy)-phenyl]2-methyl-5-amino-6-nitro-benzoquinoneimine | $C_{16}H_{18}N_4O_5$ | 163 | $-\underset{C_2H_4OH}{\overset{\vert}{N}}-H$ | | 55.48<br>55.56 | 5.24<br>5.42 | 16.18<br>15.81 | |
| XVII | N-[(4'dimethylamino-2',6'-dimethyl)phenyl]-2-methyl-5-amino-6-nitro-benzoquinoneimine | $C_{17}H_{20}N_4O_3$ | 220 | $-\underset{CH_3}{\overset{\vert}{N}}-CH_3$ | | 62.18<br>62.30 | 6.14<br>6.27 | 17.06<br>17.00 | |
| XVIII | N-[(4'-ethylcarbamyl-methyl-amino)phenyl]-2-methyl-5-amino-6-nitro-benzoquinoneimine | $C_{17}H_{19}N_5O_4$ | 140 | $-\underset{CH_2CONH_2}{\overset{\vert}{N}}-C_2H_5$ | | | | | |
| XIX | N-[(4'-ethyl, β-morpholinoethyl)amino-2'-methyl)phenyl]2-chloro-5-amino-6-nitro-benzoquinoneimine | $C_{21}H_{26}N_5O_4Cl \cdot 0.5 H_2O$ | 130 |  | | 55.14<br>55.37 | 5.90<br>6.10 | 15.31<br>14.96 | 7.76<br>(7.64<br>(7.84 |

TABLE C

Table C indicates the manner by which are prepared the indo compounds appearing in Table B. The different columns of this Table have the following meanings:

(1) number of the Example for the preparation of corresponding compounds carrying the same number in Table B;
(21) designation of the substituted aniline starting reactant having formula (II);
(22) designation of meta-amino phenol starting reactant having formula (I);
(23) molar ratio between the substituted aniline (22) and the meta-amino phenol (21). This ratio can be between 1:0.5 and 1:1.2, and preferably between 1:0.65 and 1:1.1;
(24) reaction medium. This medium is constituted by water, a lower alkanol such as ethanol, propanol or isopropanol, or even by a water-acetone mixture or a water-lower alkanol mixture, in a weight ratio of about 1:1;
(25) alkalinizing agent. The pH of the medium is alkalinized to a pH equal to or greater than 8 with the aid of a mineral or organic base, preferably ammonia, NaOH or an alkaline carbonate;
(26) oxidizing agent;
(27) molar ratio between the oxidizing agent (26) and the meta-amino phenol (22). This ratio varies generally between 1:1 to 8:1;
(28) temperature. The temperature varies between about −10° C. to +30° C. when as the aniline (formula II) there is used a

TABLE C-continued paraphenylene diamine, the duration of the reaction being in the order of 30 minutes to 3 hours. When there is employed as the compound of formula (II) a paranitrosoaniline, the temperature of the reaction varies in the order of 40° C. to the reflux temperature of the reaction mixture for a duration of about 4 hours;

(29) precipitating agent. At the end of the reaction, the "indo" compound is obtained, optionally, in the free form, as well as in the form of a precipitate by the addition of an acid such as acetic acid;

(30) Recrystallization agent. There is employed a solvent such as a lower alkyl acetate or an aqueous mixture such as a water-dimethyl formamide or water-acetone mixture.

EXAMPLES OF PROCESS FOR PREPARING COMPOUNDS OF FORMULA VII

| Example No. (1) | Substituted Aniline of Formula (II) (21) | Meta-amino phenol of Formula (I) (22) | Ratio (22:21) (23) | Medium (24) | Alkalizing Agent (25) | Oxidizing Agent (26) | Ratio (26:22) (27) | Melting Point (°C.) (28) | Release & Precipitation Agent (29) | Recrystallization Agent (30) |
|---|---|---|---|---|---|---|---|---|---|---|
| VIII | paraaminophenyl | 2-methyl-5-amino-6-nitro-phenol (compound I) | 1:1 | water | NH$_4$OH | NH$_4$ persulfate | 2:1 | 0 | acetic acid | |
| IX | 3-chloro-4-amino-phenol-hydrochloride | 2-methyl-5-amino-6-nitro-phenol (compound I) | 1:1 | water | NH$_4$OH | potassium ferricyanide | 4:1 | 0 | acetic acid | (water-dimethyl-formamide) |
| X | 2-methoxy-5-methyl-paraphenylene-diamene-di-hydrochloride | 2-methyl-5-amino-6-nitro-phenol (compound I) | 1:1 | (water-acetone) | NH$_4$OH | potassium ferricyanide | 4:1 | 0 | | (water-dimethyl-formamide) |
| XI | 2,5-dimethyl-paraphenylene-diamine-di-hydrochloride | 2-methyl-5-amino-6-nitro-phenol (compound I) | 1:1 | (water-acetone) | NH$_4$OH | NH$_4$ persulfate | 2:1 | 0 | | (water-dimethyl-formamide) |
| XII | 2,5-dimethyl-paraphenylene-diamine-di-hydrochloride | 2-methyl-5-acetylamino-6-nitro-phenol (compound V) | 1:1 | water | NH$_4$OH | NH$_4$ persulfate | 2:1 | 0 | acetic acid | (water-dimethyl-formamide) |
| XIII | chloro-paraphenylene-diamine hydrochloride | 2-methyl-5-amino-6-nitro-phenol (compound I) | 1:1 | (water-isopropanol) | NH$_4$OH | potassium ferricyanide | 4:1 | 0 | | (water-dimethyl-formamide) |
| XIV | 2,5-dimethyl-2,5-paraphenylene-diamine-di-hydrochloride | 2-methyl-5-carbethoxy-6-nitro-6-phenol (compound VI) | 1:1 | (water-acetone) | NH$_4$OH | NH$_4$ persulfate | 2:1 | 0 | acetic acid | ethyl acetate |
| XV | 2-chloro-4-amino-methyl-aniline-sulfate | 2-methyl-5-amino-6-nitro-phenol (compound I) | 1:1 | (water-isopropanol) | NH$_4$OH | potassium ferricyanide | 4:1 | 0 | | (water-dimethyl-formamide) |
| XVI | 2-methoxy-amino-N, β-hydroxy-ethyl-aniline-sulfate | 2-methyl-5-amino-6-nitro-phenol (compound I) | 1:1.1 | (water-acetone) | NH$_4$OH | H$_2$O$_2$ | 8:1 | ambiant | | (water-dimethyl-formamide) |
| XVII | 3,5-dimethyl-4-amino-N,N-dimethyl-aniline-di-hydrochloride | 2-methyl-5-amino-6-nitro-phenol (compound I) | 1:1 | (water-isopropanol) | NH$_4$OH | potassium ferricyanide | 4:1 | 0 | | (water-dimethyl-formamide) |
| XVIII | 4-amino-N,N-ethylcarbamyl-methyl-aniline | 2-methyl-5-amino-6-nitro-phenol (compound I) | 1:1 | (water-acetone) | NH$_4$OH | H$_2$O$_2$ | 8:1 | ambiant | | (water-dimethyl-formamide) |
| XIX | 3-paranitroso-methyl-N,N(ethyl, morpholino-ethyl)-aniline-di-hydrochloride | 2-chloro-5-amino-6-nitro-phenol (compound IV) | 1:1 | (water-ethanol) | NaOH | | | 50 | | (water-acetone) |

To illustrate in a complete manner the process for preparing the "indo" compounds of Table C, there is reproduced below on the one hand Examples VIII, XII, XIV and XVI using as the initial reactant a paraphenylenediamine and on the other hand, Example XIX using as the initial reactant a paranitrosoaniline.

EXAMPLE NO. VIII

Preparation of N-[(4'-hydroxy)phenyl]-2-methyl-5-amino-6-nitro benzoquinoneimine

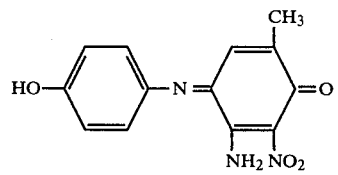

0.01 mole (1.09 g) of para-amino-phenol and 0.01 mole (1.68 g) of 2-methyl-5-amino-6-nitro phenol are dissolved in 15 cc of ammonia (22° Bé) to which have been added 15 cc of water. To this resulting solution maintained at a temperature of about 0° C., there is added, with agitation, 0.02 mole (4.6 g) of ammonium persulfate in 20 cc of water. The agitation is maintained for 30 minutes, after which the indophenol which has precipitated in the form of its ammonium salt is filtered.

The thus recovered crude product is treated with water to which has been added acetic acid to obtain the indophenol in its free form. After filtering the indophenol, washing it with water and drying it under a vacuum, there is obtained a product which melts with decomposition above 260° C.

| Elemental analysis: $C_{13}H_{11}N_3O_4$ | | |
|---|---|---|
| | Calculated | Theory |
| C% | 57.14 | 57.13 |
| H% | 4.06 | 4.22 |
| N% | 15.38 | 15.16 |

EXAMPLE NO. XVI

Preparation of N-[(4'-β-hydroxyethylamino-3'-methoxy)phenyl]-2-methyl-5-amino-6-nitro benzoquinoneimine

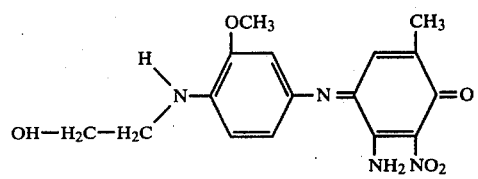

0.01 mole (1.68 g) of 2-methyl-5-amino-6-nitro phenol and 0.011 mole (3.08 g) of 2-methoxy amino N,β-hydroxyethylaniline are dissolved in 40 cc of a 50% hydroacetonic solution, and 20 cc of ammonia (22° Bé). There are then added 50 cc of $H_2O_2$ (20 volumes), and the reaction mixture is permitted to stand for 3 hours at ambient temperature. The desired indoaniline which has precipitated is then filtered, washed with water, recrystallized in a mixture of dimethyl formamide and water and dried under a vacuum. The product melts at 163° C.

| Elemental analysis: $C_{16}H_{18}N_4O_2$ | | |
|---|---|---|
| | Calculated | Found |
| C% | 55.48 | 55.56 |
| H% | 5.24 | 5.42 |
| N% | 16.18 | 15.81 |

EXAMPLE NO. XIX

Preparation of N-[(4'-ethyl, β-morpholinoethylamino-2'-methyl)phenyl]-2-chloro-5-amino-6-nitro benzoquinoneimine

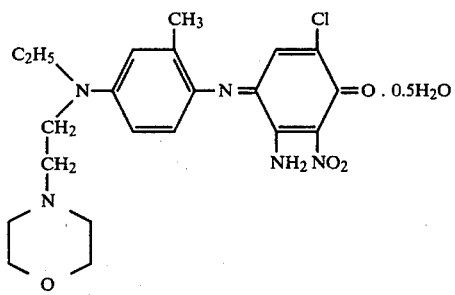

0.01 mole (1.88 g) of 2-chloro-5-amino-6-nitro phenol and 0.01 mole (3.50 g) of 3-paranitroso methyl-N,N-(ethyl, morpholinoethyl) aniline are introduced into 20 cc of a normal NaOH solution to which have been added 20 cc of ethanol. The resulting reaction mixture is maintained for 4 hours at 50° C. The desired indoaniline which precipitates in crystalline form, is filtered, washed with a 50% hydroalcoholic solution, recrystallized initially in a hydroacetonic solution and then in a dimethylformamide-water mixture, and dried under a vacuum. The product obtained melts at 130° C.

| Elemental analysis: $C_{21}H_{26}N_5O_4Cl \cdot 0.5H_2O$ | | |
|---|---|---|
| | Calculated | Found |
| C% | 55.14 | 55.37 |
| H% | 5.90 | 6.10 |
| N% | 15.31 | 14.96 |
| Cl% | 7.76 | 7.64-7.84 |

EXAMPLE NO. XII

Preparation of N-[(4'-amino-2',5'-dimethyl)phenyl]-2-methyl-5-acetylamino-6-nitro benzoquinoneimine.

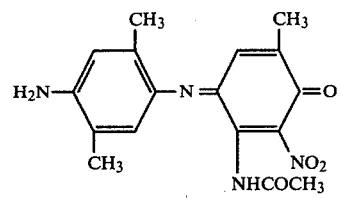

0.02 mole (4.2 g) of 2-methyl-5-acetylamino-6-nitro phenol and 0.02 mole (4.18 g) of 2,5-dimethyl paraphenylenediamine dihydrochloride are dissolved in 15 cc of acetone, 30 cc of water and 25 cc of ammonia (22° Bé). To this solution, maintained at a temperature of about 0° C., there is added, with agitation, 0.04 mole (9.2 g) of ammonium persulfate in 30 cc of water. Agitation of the resulting mixture is maintained for 30 minutes at which point there is added an amount of acetic acid necessary to precipitate the desired indoaniline, which is then filtered, washed with water, recrystallized in a dimethylformamide-water mixture and dried under a vacuum at 60° C. The product melts with decomposition at 235° C.

| Elemental analysis: $C_{17}H_{18}N_4O_4$ | | |
|---|---|---|
| | Calculated | Found |
| C% | 59.64 | 59.84 |
| H% | 5.30 | 5.42 |
| N% | 16.37 | 16.10 |

EXAMPLE NO. XIV

Preparation of N-[(4'-amino-2',5'-dimethyl)phenyl]-2-methyl-5-carbethoxyamino-6-nitro benzoquinoneimine.

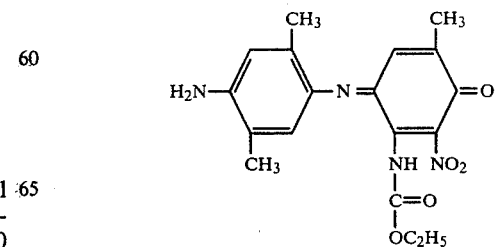

0.01 mole (2.40 g) of 2-methyl-5-carbethoxyamino-6-nitro phenol is dissolved in 30 cc of a 50% hydroacetonic solution and 6 cc of ammonia (22° Bé). To the resulting solution, maintained at a temperature of about 0° C., there are added, little by little, simultaneously with the use of a double funnel, and with agitation, 0.01 mole (2.09 g) of 2,5-dimethyl paraphenylenediamine dihydrochloride in 25 cc of water, and 0.02 mole (4.6 g) of ammonium persulfate in 25 cc of water. As soon as the additions are completed, there are added 5 cc of acetic acid to the reaction mixture. The desired indoaniline which precipitates is filtered, washed with water and recrystallized in ethyl acetate. The product melts at 242° C.

| Elemental analysis: $C_{18}H_{20}N_4O_5$ | | |
| --- | --- | --- |
| | Calculated | Found |
| C % | 58.06 | 57.86 |
| H % | 5.41 | 5.60 |
| N % | 15.05 | 15.16 |

TABLE D

This Table describes the Examples illustrating the various dye compositions of the present invention containing at least one compound of formula I, used as a direct dye or as an oxidation dye, optionally in the presence of another coupler or another direct dye, in an appropriate carrier.

Compositions Nos. 1-7 correspond to the use of the compounds of the present invention as direct dyes.

Compositions Nos. 8-20 correspond to their use both as an oxidation dye and as a direct dye since there is a molar excess of coupler relative to the oxidation base.

Compositions Nos. 21-79 correspond to their use only as an oxidation dye, the molar quantity of the couplers being equal to or lower than that of the oxidation base.

Columns (31) to (48) of this Table have the following meanings:

(31) number of the Example of the composition;
(32), (33), (34) these columns indicate, respectively, the number of the coupler of the present invention (I to VIII) with the designation of another optional coupler (C1 to C10); and for 100 g of the composition, the amount in moles per 100 grams and grams per 100 grams;
(35), (36), (37) these columns indicate respectively the designation of the oxidation base (B1 to B36) as well as for 100 g of the composition, the amount in mole per 100 g and in grams per 100 g;
(38), (39), (40) these columns indicate respectively another direct dye (CD1 to CD5); and for 100 g of the composition the amount in moles per 100 g and in grams per 100 g.
(41) ratio of coupler:oxidation base;
(42) to (47) these columns indicate the composition of the carrier with the designation and the weight in gram percent, respectively, for solvents (42) (43); surface active agents (44) (45); and other adjuvants (46) (47). When the solvent is water, it is not mentioned in this Table;
(48) pH of the composition. When no particular mention appears in the above pH values, it is obtained by the addition of an ammonia solution.

It is understood that for each of the compositions, the complement to 100 g is obtained by the addition of water.

EXAMPLES OF DYE COMPOSITIONS CONTAINING AT LEAST:
- EITHER A COMPOUND OF FORMULA (I)
- OR A COMPOUND OF FORMULA (I) AND A COMPOUND OF FORMULA (II)

| Composition No. (31) | Coupler of Formula (I) and Other Couplers No. (32) | mole % (33) | Wt. g % (34) | Oxidation Base of Formula (II) and Other Bases Name (35) | mole % (36) | Wt. g % (37) | Other Direct Dyes Name (38) | mole % (39) | Wt. g % (40) | Coupler/ Oxidation Base (41) | Solvents Name (42) | Wt. g % (43) | Surface Active Agents Name (44) | Wt. g % (45) | Other Adjuvants Name (46) | Wt. g % (47) | pH (48) |
|---|---|---|---|---|---|---|---|---|---|---|---|---|---|---|---|---|---|
| 1 | I | | 0.2 | | | | | | | | ET | 20 | | | CMC | 4 | 9 |
| 2 | II | | 0.2 | | | | | | | | ET | 25 | | | CMC | 3 | 10. |
| 3 | IV | | 0.5 | | | | CD1 | | 0.5 | | BG | 5 | AL 10.5 OE | 5 | | | 9.6 |
| 4 | IV | | 0.7 | | | | CD2 | | 1 | | BG | 25 | | | CMC | 3.75 | 9.5 |
| | | | | | | | CD3 | | 0.5 | | | | | | | | |
| 5 | III | | 0.1 | | | | | | | | | | | | | | 9.6 |
| 6 | VI | | 2.0 | | | | | | | | BG | 20 | | | | | 9 |
| 7 | V | | 1.0 | | | | | | | | | | | | | | |
| 8 | I | 0.006 | 1.008 | B1 | 0.002 | 0.682 | | | | 3 | | | AL 10.5 OE | 20 | | | 9 |
| 9 | I | 0.0148 | 2.5 | B2 | 0.00113 | 0.3 | | | | 2 | PG | 30 | NP 4OE | 20 | | | 10.3 |
| | | | | | | | | | | | | | NP 9OE | 20 | | | |
| C1 | | 0.00199 | 0.3 | B3 | 0.0078 | 1.5 | | | | | | | AL 10.5 OE | 20 | | | 10 |
| | | | | | | | | | | | | | NP 4OE | 7 | | | |
| | | | | | | | | | | | | | NP 9OE | 7 | | | |
| 10 | I | 0.0015 | 0.25 | B4 | 0.001 | 0.29 | | | | 3/2 | ET | 20 | | | CMC | 4 | 10.8 |
| 11 | I | 0.0075 | 1.26 | B5 | 0.005 | 1.035 | | | | 3/2 | ET | 25 | | | CARBOPOL 934 | 3.36 | 10.3 |
| 12 | I | 0.006 | 1.008 | B6 | 0.003 | 0.813 | | | | 2 | ET | 20 | NP 4OE | 16 | | | 9.5 (TEA) |
| | | | | | | | | | | | | | NP 9OE | 16 | | | |
| 13 | II | 0.006 | 1.272 | B7 | 0.003 | 0.585 | | | | 2 | | | LSA | 5 | | | 10.5 |

TABLE D-continued

| Ex. | Col A | Col B | Col C | Col D | Col E | Col F | Col G | Col H | Col I | Col J | Col K | Col L | Col M | Col N |
|---|---|---|---|---|---|---|---|---|---|---|---|---|---|---|
| 14 | II | 0.012 | 2.544 | B2 | 0.003 | 0.792 | 3/2 | | | 7.5 | DAGC | | | 10 |
|  | C2 | 0.004 | 0.612 | B8 | 0.003 | 0.585 |  |  |  |  |  |  |  |  |
|  |  |  |  | B9 | 0.005 | 0.545 |  |  |  |  |  |  |  |  |
| 15 | II | 0.010 | 2.12 | B10 | 0.010 | 1.195 | 3 | BG | 30 | 2.8 | AO2OE | | | 10.3 |
|  | C1 | 0.003 | 0.5 | B9 | 0.0025 | 1.09 |  |  |  | 4.2 | AO4OE |  |  |  |
|  | C3 | 0.040 | 0.436 | B11 | 0.0005 | 0.562 |  |  |  |  |  |  |  |  |
| 16 | IV | 0.0037 | 0.7 | B12 | 0.005 | 0.15 | 4/3 | ET | 25 | 7.5 | DAGC | | | 10 |
|  | C4 | 0.0024 | 0.4 | B13 | 0.0036 | 0.17 |  |  |  |  |  |  |  |  |
|  |  |  |  | B14 | 0.0015 | 0.5 |  |  |  |  |  |  |  |  |
| 17 | IV | 0.006 | 1.13 | B13 |  | 0.49 | 4 |  |  | 5 | AL 10.5 OE | | | 10.2 |
|  |  |  |  |  |  |  |  |  |  | 15 | ASA |  |  |  |
| 18 | III | 0.004 | 0.728 | B15 | 0.001 | 0.211 | 4 | PG | 7.4 | 2.8 | AO2OE | | | 10.8 |
|  |  |  |  |  |  |  |  |  |  | 4.2 | AO4OE |  |  |  |
| 19 | I | 0.005 | 0.84 | B8 | 0.001 | 0.195 | 5 | PG | 40 |  |  |  |  | 10 |
| 20 | VII |  | 0.84 | B17 |  | 0.317 |  |  |  | 20 | LSS 19 | | | 10 |
| 21 | C5 | 0.0025 | 0.38 | B18 | 0.0025 | 0.49 | 1 | ET | 40 |  |  | CARBOPOL 934 | 2.7 | 10.5 |
| 22 | II | 0.006 | 0.636 | B19 | 0.003 | 0.735 | 2 | PG | 20 |  |  | Trilon B | 0.2 | 10.5 |
|    |    |    |    |    |    |    |    |    |    |    |    | BS | 1.0 |    |
| 23 | I | 0.003 | 0.504 | B9 | 0.003 | 0.327 | 1 | | | 20 | LSS 19 | CARBOPOL 934 | 3.6 | 10.5 |
| 24 | I | 0.001 | 0.168 | B8 | 0.001 | 0.195 | 1 | | | 20 | LSS 19 | EDTA | 0.2 | 10.5 |
| 25 | I | 0.004 | 0.672 | B8 | 0.004 | 0.195 | 1 | | | 20 | LSS 19 | EDTA | 0.2 | 10.5 |
|    |    |    |    | B9 | 0.003 | 0.327 |    |    |    |    |    | EDTA | 0.2 |    |
|    |    |    |    |    |    |    |    |    |    |    |    | BS | 1.0 |    |
| 26 | I | 0.004 | 0.672 | B8 | 0.003 | 0.585 | 1 | | | 20 | LSS 19 | EDTA | 0.2 | 10.5 |
|    |    |    |    | B9 | 0.003 | 0.209 |    |    |    |    |    | BS | 1.0 |    |
| 27 | I | 0.004 | 0.672 | B20 | 0.003 | 0.327 | 1 | | | 20 | LSS 19 | EDTA | 0.2 | 10.5 |
|    |    |    |    | B9 | 0.003 | 0.627 |    |    |    |    |    | BS | 1.0 |    |
| 28 | I | 0.004 | 0.672 | B20 | 0.003 | 0.109 | 1 | | | 20 | LSN | EDTA | 0.2 | 10.5 |
|    |    |    |    | B9 | 0.001 | 0.68 |    |    |    |    |    | BS | 1.0 |    |
| 29 | I | 0.0025 | 0.42 | B6 | 0.0025 | 0.18 | 1 | | | 20 | LSS 19 | Trilon B | 0.2 | 10.3 |
|    |    |    |    |    |    | 0.50 |    |    |    |    |    | BS | 1.0 |    |
| 30 | I | 0.0044 | 0.75 | B21 | 0.0012 | 0.125 | 0.95 | | | 20 | LSS 19 | Trilon B | 0.2 | 10.7 |
|    | C1 | 0.0016 | 0.25 | B9 | 0.0046 | 0.717 |    |    |    |    |    | BS | 1.0 |    |
|    |    |    |    | B22 | 0.0006 | 0.109 |    |    |    |    |    |    |    |    |
| 31 | I | 0.004 | 0.672 | B10 | 0.003 | 0.682 | 1 | | | 20 | LSS 19 | EDTA | 0.2 | 10.4 |
|    |    |    |    | B9 | 0.001 | 0.2 |    |    |    |    |    | BS | 1.0 |    |
| 32 | I | 0.002 | 0.336 | B1 | 0.002 | 0.5 | 1 | | | 20 | AL 10.5 OE | | | 10.4 |
|    |    |    |    |    |    |    |    |    |    | 15 | ASA |    |    |    |
| 33 | I | 0.003 | 0.5 | B11 | 0.0009 | 0.135 | 1 | | | 5 | AL 10.5 OE | | | 10.2 |
|    | C1 | 0.00165 | 0.25 | B9 | 0.0046 | 0.18 |    |    |    | 20 | LSS 19 |    |    |    |
| 34 | I | 0.0045 | 0.75 | B11 | 0.0006 | 0.5 | 1 | | | | | Trilon B | 0.2 | 10.8 |
|    | C1 | 0.00165 | 0.25 | B21 | 0.00126 | 0.6 |    |    |    |    |    | BS | 1.0 |    |
|    |    |    |    | B9 | 0.0046 | 0.5 |    |    |    |    |    |    |    |    |
| 35 | I | 0.0059 | 1 | B8 | 0.003 | 1.2 | 1 | BG | 25 |  |  | CARBOPOL 934 | 3.5 | 10.6 |
|    | C6 | 0.0045 | 0.5 | B37 | 0.00155 | 0.126 |    |    |    |    |    |    |    |    |
|    | C3 | 0.0045 | 0.5 | B9 | 0.011 | 0.5 |    |    |    |    |    |    |    |    |
| 36 | I | 0.00357 | 0.6 | B15 | 0.00059 | 0.225 | 1 | BG | 5 | 5 | AL 10.5 OE | | | 10.7 |
|    | C1 | 0.00165 | 0.25 | B9 | 0.00458 |  |    |    |    |    |    |    |    |    |
| 37 | I | 0.001 | 0.168 | B11 | 0.001 |  | 1 | | | 20 | LSS 19 | EDTA | 0.2 | 10.3 |
|    |    |    |    |    |    |    |    |    |    |    |    | BS | 1.0 |    |
| 38 | I | 0.004 | 0.672 | B11 | 0.001 | 0.225 | 1 | | | 20 | LSS 19 | EDTA | 0.2 | 10.4 |
|    |    |    |    | B9 | 0.003 | 0.327 |    |    |    |    |    |    |    |    |
| 39 | I | 0.004 | 0.672 | B7 | 0.001 | 0.195 | 1 | | | 20 | LSS 19 | EDTA | 0.2 |    |

TABLE D-continued

| | | | | | | | | | | | | | |
|---|---|---|---|---|---|---|---|---|---|---|---|---|---|
| 40 | I | 0.004 | 0.672 | B9 B23 | 0.003 0.001 | | 0.327 0.225 | | | | | BS EDTA | 1.0 0.2 | 10.4 |
| | | | | B9 | 0.003 | | 0.327 | | | | | BS | 1.0 | 10.4 |
| 41 | I | 0.00178 | 0.3 | B8 | 0.0014 | | 2 | | PG | 35 | DAGC | 6.5 | | |
| | C1 | 0.00198 | 0.3 | B15 | 0.0008 | | 0.3 | | | | | | | |
| | C7 | 0.00365 | 0.5 | B24 | 0.0137 | | 0.2 | | | | | | | |
| | C2 | 0.00651 | 1 | B9 | 0.003 | | 1.5 | | | | | | | 8.8 |
| 42 | I | 0.004 | 0.672 | B21 | 0.001 | | 0.4275 0.109 | | | | LSS 19 | 20 | Trilon B BS | 0.2 1.0 | 10.8 8 |
| 43 | I | 0.0089 | 1.5 | B25 B26 | 0.00078 0.00126 | | 0.2 0.25 | | BG | 25 | NP 4OE NP 9OE | 15 15 | | | |
| | | | | B9 | 0.0091 | | 1 | 0.8 | | | | | | | |
| 44 | I | 0.004 | 0.672 | B27 | 0.004 | | 0.78 | | BG | 5 | LSA | 5 | | | 9 |
| 45 | I | 0.006 | 1.008 | B28 | 0.006 | | 2.136 | | ET | 30 | AL 10.5 OE | 5 | | | 8.5 |
| 46 | I | 0.005 | 0.84 | B29 | 0.005 | | 1.22 | | | | DAGC | 7 | | | 6 (AL) |
| 47 | I | 0.00089 | 0.15 | B21 | 0.0025 | | 0.36 | | PG | 30 | NP 4OE | 17 | | | 10 |
| | C1 | 0.00265 | 0.4 | B11 | 0.0012 | | 0.27 | | | | NP 9OE | 17 | | | |
| 48 | C2 | 0.00287 | 0.44 | B9 | 0.009 | | 1 | | BG | 5 | AL 10.5 OE | 5 | | | 9.6 |
| 49 | I | 0.0015 | 0.25 | B30 | 0.003 | | 0.84 | | PG | 40 | DAGC | 6 | | | 8.5 |
| | I | 0.0357 | 0.6 | B10 | 0.00418 | 0.15 0.5 | 1 | 0.85 | | | | | | | |
| 50 | I | 0.00029 | 0.05 | B8 | 0.00029 | | 0.057 | | ET | 5 | LSS 19 | 20 | EDTA | 0.2 | 10 |
| 51 | I | 0.001 | 0.168 | B2 | 0.001 | | 0.264 | | | | | | BS | 1.0 | 10.5 |
| 52 | I | 0.004 | 0.672 | B2 | 0.001 | | 0.264 | | | | LSS 19 | 20 | EDTA | 0.2 | 10.5 |
| | | | | B9 | 0.003 | | 0.327 | | | | | | BS | 1.0 | |
| 53 | I | 0.004 | 0.672 | B31 | 0.004 | | 1.3 | | PG | 7.4 | AO2OE AO4OE | 3.7 5.5 | | | |
| 54 | I | 0.002 | 0.336 | B32 | 0.002 | | 0.528 | | EMDG | 10 | | | CARBOPOL 934 | 3.35 | 8 (TEA) |
| 55 | I | 0.0015 | 0.252 | B18 | 0.0015 | | 0.289 | | ET | 25 | | | | | 10.5 |
| 56 | I | 0.0089 | 1.5 | B21 | 0.0025 | | 0.36 | | | | LSS 19 | 20 | EDTA | 0.2 | 8.5 |
| | C1 | 0.00265 | 0.4 | B9 | 0.009 | | 1 | 0.9 | | | | | BS | 1.0 | 10.5 |
| | | | | B11 | 0.0012 | | 0.27 | | | | | | | | |
| 57 | I | 0.0089 | 1.5 | B21 | 0.0025 | | 0.36 | | | | LSS 19 | 20 | EDTA | 0.2 | 10.5 |
| | C1 | 0.00265 | 0.4 | B9 | 0.009 | | 1 | 0.9 | | | | | BS | 1.0 | |
| | | | | B8 | 0.0012 | | 0.234 | | | | | | | | |
| 58 | I | 0.0000119 | 0.002 | B32 | 0.0000119 | | 0.0023 | | ET | 20 | LSA | 5 | Trilon B | 0.2 | 10 |
| 59 | II | 0.003 | 0.636 | B7 | 0.003 | | 0.585 | 1 | | | LSS 19 | 20 | BS | 1.0 | 10.5 |
| 60 | II | 0.001 | 0.212 | B8 | 0.001 | | 0.195 | 1 | | | | | | | 10.6 10.5 |
| 61 | II | 0.01 | 2.12 | B33 | 0.01 | | 2.58 | 1 | EG | 20 | NP 4OE NP 9OE | 8 8 | CMC | 3.75 | 9.5 |
| 62 | II C3 | 0.005 0.005 | 1.06 0.545 | B9 B21 B10 B9 | 0.005 0.003 0.006 0.003 | | 0.545 0.428 1.43 0.327 | 1 | PG | 25 | | | | | |
| 63 | IV | 0.003 | 0.565 | B9 | | | | | | | LSS 19 | 20 | EDTA BS | 0.2 1.0 | 10.5 |
| 64 | IV | 0.004 | 0.753 | B8 B9 | 0.002 0.002 | | 0.39 0.218 | 1 | | | LSS 19 | 20 | EDTA BS | 0.2 1.0 | 10.5 10.5 |
| 65 | IV | 0.004 | 0.753 | B11 | 0.001 | | 0.225 | | | | LSS 19 | 20 | EDTA | 0.2 | |

TABLE D-continued

| | | | | | | | | | | | |
|---|---|---|---|---|---|---|---|---|---|---|---|
| 66 | IV | 0.006 | 1.13 | B9<br>B24 | 0.003<br>0.006 | 0.327<br>1.5 | | | | BS<br>CMC | 1.0<br>4 | 10.5<br>7<br>(TEA) |
| 67 | IV | 0.0025 | 0.47 | B6 | 0.0025 | 0.68 | | 1 | | Trilon B<br>BS | 0.2<br>1.0 | 10.5<br>10.2 |
| 68 | IV<br>C8 | 0.00796<br>0.00164 | 1.5<br>0.3 | B11<br>B19<br>B34 | 0.00178<br>0.00204<br>0.00588 | 0.4<br>0.5<br>1.2 | PG | 1 | 25 | LSN | 20 | 10.2 |
| 69 | IV | 0.0015 | 0.283 | B13 | 0.0015 | 0.491 | | 1 | 7.5 | DAGC | | |
| 70 | IV<br>C4 | 0.00795<br>0.0048 | 1.5<br>0.8 | B18<br>B5<br>B35 | 0.002<br>0.0048<br>0.00549 | 0.4<br>1.0<br>1.0 | BG | ¼ | 30 | ASA<br>AL 10.5 OE<br>AO2OE<br>AO4OE | 15<br>2.8<br>4.2 | 9 |
| 71 | IV<br>C9<br>C6<br>C10 | 0.00265<br>0.009<br>0.001 | 0.5<br>0.25<br>1<br>0.4<br>0.182 | B9<br>B36<br>B9<br>B33<br>B30<br>B15 | 0.0137<br>0.001 | 1.5<br>0.5<br>1.4<br>0.8<br>0.3<br>0.211 | PG | | 30 | CARBOPOL<br>934 | 3.6 | 8.8 |
| 72 | III | 0.001 | 0.182 | B15 | 0.001 | 0.211 | PG | 1 | 7.4 | | | 10.7 |
| 73 | III<br>C3 | 0.005<br>0.005 | 0.91<br>0.545 | B9<br>B8 | 0.006<br>0.006 | 0.654<br>1.17 | PG | 0.8 | 25 | AO2OE<br>AO4OE<br>NP 4OE<br>NP 9OE | 2.8<br>4.2<br>17.5<br>17.5 | CD1 0.2 10 |
| 74 | III<br>C2 | 0.003<br>0.003 | 0.546<br>0.46 | B22<br>B9 | 0.002<br>0.005 | 0.418<br>0.545 | BG | 0.85 | 30 | LSA | 7 | CD4 0.1 10.2 |
| 75 | V | 0.005 | 1.05 | B2 | 0.005 | 1.32 | PG | 1 | 20 | AO2OE<br>AO4OE | 3.2<br>4.8 | 10 |
| 76 | VI | 0.003 | 0.72 | B7 | 0.003 | 0.585 | BG | 1 | 5 | AL 10.5 OE | 5 | 10.5 |
| 77 | V | 0.004 | 0.84 | B9 | 0.004 | 0.436 | BG | 1 | 20 | DAGC | 8 | 9.5 |
| 78 | I | 0.001 | 0.168 | B8 | 0.005 | 0.975 | PG | 1/5 | 40 | CARBOPOL<br>934 | 2.7 | 10.5 |
| 79 | I | 0.002 | 0.336 | B15 | 0.001 | 0.211 | ET | 2 | 10 | LSS 19 | | 10.5 |

C1 = 6-hydroxy-phenomorpholine
C2 = 3-N,β-hydroxy-ethylamino-phenol
C3 = Meta-aminophenol
C4 = 2-methyl-5-N,β-hydroxyethylamino-phenol

LEGEND OF TABLE D
Couplers of Column (32) Other Than the Couplers of Formula (I)
C5 = 2-nitro-3-amino-phenol
C6 = resorcinol
C7 = 2,6-dimethyl-3-amino-phenol C8 = 2-methoxy-5-N,β-hydroxyethylamino-phenol
C9 = 2,4-diamino-anisole-dihydrochloride
C10 = 2-methyl-5-acetylamino-phenol Bases in Column (35)

B1 = 2-methyl-4-amino-N-mesylaminoethylaniline-sulfate
B2 = 3-methoxy-4-amino-N,N-dimethylaniline-sulfate
B3 = 2,6-dimethyl-4-amino-phenol
B4 = 4-amino-N-acetylamino-ethylaniline-sulfate
B5 = 3-methyl-4-amino-N-ethylcarbamylmethylaniline
B6 = 3-methyl-4-amino-N,N-ethyl, mesylaminoethylaniline
B7 = N-methylparaphenylenediamine-dihydrochloride
B8 = paratoluylenediamine-dihydrochloride
B9 = para-amino-phenol
B10 = 2,6-dimethyl-3-methoxy-paraphenylenediamine-dihydrochloride
B11 = 2-methyl-5-methoxy-paraphenylenediamine-dihydrochloride
B12 = 2-methoxy-4-amino-N,β-hydroxyethylaniline-sulfate B13 = 4-amino-N-mesylaminoethylaniline-sulfate
B14 = 2,5-dimethyl-4-amino-phenol
B15 = methoxyparaphenylenediamine-dihydrochloride
B17 = methoxyparaphenylenediamine-dihydrochloride
B18 = 4-amino-N,N-ethyl, carbamylmethylaniline
B19 = 4-amino-N,N-di-β-hydroxyethylaniline-sulfate
B20 = N,N-dimethylparaphenylenediamine-dihydrochloride
B21 = chloroparaphenylenediamine
B22 = 3-methyl-4-amino-N,N-methylaniline-dihydrochloride
B23 = 3-methoxy-4-amino-N-methylaniline-dihydrochloride
B24 = 4-amino-N,β-hydroxyethylaniline-sulfate
B25 = 2-chloro-4-amino-N-methylaniline-sulfate B26 = 2-methyl-4-amino-N-methylaniline-sulfate
B27 = 2-methoxy-4-amino-N,carbamylmethylaniline
B28 = 4-amino-N,N-ethyl,β-piperidino-ethylaniline-trihydrochloride
B29 = 4-amino-N,N-ethyl,β-sulfo-ethylaniline
B30 = 3-methoxy-4-amino-N,β-hydroxyethylaniline-sulfate
B31 = 2-chloro-4-amino-N,β-acetylaminoethylaniline-sulfate
B32 = 2-methyl-4-amino-N,β-hydroxyethylaniline-sulfate
B33 = 3-methyl-4-amino-N-ethyl,β-sulfoethylaniline
B34 = 3-methyl-4-amino-phenol-hydrobromide
B35 = 2,5-diamino-pyridine-dihydrochloride
B36 = 2,4-dihydroxy-5,6-diamino-pyrimidine-sulfate
B37 = 4-amino-2-methoxy-N-acetylaminoethylaniline-sulfate Other Direct Dyes of Column (38)

TABLE D-continued

CD1 = 4-nitro-5-N-methylamino)phenyl carboxymethylether
CD2 = 3-nitro-4-N'-methylamino-N,N methyl,β-hydroxyethylanlline
CD3 = tetra-amino-anthraquinone
CD4 = nitro-metaphenylenediamine
CD5 = 3-methoxy-4,6-diamino-4'-hydroxy-diphenylamine-trihydrochloride Carriers Corresponding to the Compounds in Columns (42) (44) (46) and pH Adjustment Agent (48)

| | | | |
|---|---|---|---|
| ET | = ethanol | CARBOPOL 934 | = polymer of acrylic acid, having a molecular weight between 2 and 3 million |
| CMC | = carboxymethylcellulose | LSA | = ammonium lauryl sulfate |
| EG | = ethylglycol | TEA | = triethanolamine |
| AL 10.5 OE | = lauryl alcohol oxyethylenated with 10.5 moles of ethyleneoxide | DAGC | = diethanolamides of the fatty acids of copra |
| NP 4OE | = nonylphenol oxyethylenated with 4 moles of ethyleneoxide | AO 2OE | = oleyl alcohol oxyethylenated with 2 moles of ethyleneoxide |
| NP 9OE | = nonylphenol oxyethylenated with 9 moles of ethyleneoxide | AO 4OE | = oleyl alcohol oxyethylenated with 4 moles of ethyleneoxide |
| PG | = propyleneglycol | ASA | = ammonium alkyl sulfate wherein the alkyl moiety is $C_{12}$-$C_{14}$ (70% $C_{12}$-30% $C_{14}$) |
| | | LSS 19 | = mixture of 19% lauryl alcohol oxyethylenated with 2 moles of ethyleneoxide and 81% of the sodium sulfate salt of this same oxyethylenated alcohol |
| | | EDTA | = Trilon B = ethylenediamine tetracetic acid |
| | | BS | = 40 wt. % solution of sodium disulfide |
| | | EMDG | = monomethylether of diethyleneglycol |
| | | EG | = ethylglycol |
| | | LSN | = sodium lauryl sulfate |
| | | AL | = lactic acid |

TABLE E

This Table describes some Examples illustrating the process for preparing and using dyes T1 to T78 carried out with the aid of compositions 1 to 79 of Table D. Columns (51) to (58) have the following meanings:

(51) number of the Example of dyeing;
(31) number of the Example of the composition used for the dyeing;
(52) quantity in grams of the composition;
(53) name of the oxidizing agent;
(54) quantity in grams of the oxidizing agent used;
(55) nature of the hair treated;
(56) temperature of application in °C.;
(57) duration of the application in minutes;
(58) color obtained.

Remark: One can dye in accordance with the present invention naturally white hair, completely or partially bleached hair, or even natural hair containing no white hair.

EXAMPLES OF PROCESS FOR DYEING HAIR WITH THE COMPOSITIONS OF TABLE D

| Dye No. (51) | Composition Example No. (31) | Quantity (g.) (52) | Oxidizing Agent Added Name (53) | Amount (54) | Hair Treated (55) | Application Temperature (°C.) (56) | Contact Time (mn.) (57) | Coloration (58) |
|---|---|---|---|---|---|---|---|---|
| T1  | 1  |     |                          |     | D (J) | A  | 20 | Light salmon |
| T2  | 2  |     |                          |     | D     | A  | 20 | Rose eglantine |
| T3  | 3  |     |                          |     | D     | 30 | 20 | Very luminous salmon pink |
| T4  | 4  |     |                          |     | D     | A  | 5  | Silver grey with light mauve glints |
| T5  | 5  |     |                          |     | D     | A  | 20 | Pink champagne |
| T6  | 6  |     |                          |     | D     | 35 | 20 | Pink apricot |
| T7  | 7  |     |                          |     | D     | 30 | 20 | Very luminous topaz |
| T8  | 8  | 100 | $H_2O_2$(20 vol.) | 40  | N | A  | 20 | Silvery grey-violet |
| T9  | 9  | 100 | $H_2O_2$(20 vol.) | 75  | N | 30 | 15 | Ash beige |
| T10 | 10 | 100 | $H_2O_2$(20 vol.) | 60  | N | 20 | 25 | Silver grey with mauve glints |
| T11 | 11 | 100 | $H_2O_2$(20 vol.) | 100 | N | A  | 25 | Very dark slight violet grey blue |
| T12 | 12 | 100 | $H_2O_2$(20 vol.) | 100 | N | 20 | 10 | Silvery eucalyptus green |
| T13 | 13 | 100 | $H_2O_2$(20 vol.) | 100 | D | A  | 20 | Dark violet blue |
| T14 | 14 | 100 | $H_2O_2$(20 vol.) | 70  | N | A  | 25 | Very dark grey with light violet glints |
| T15 | 15 | 100 | $H_2O_2$(20 vol.) | 70  | N | A  | 20 | Tin grey |
| T16 | 16 | 100 | $H_2O_2$(20 vol.) | 50  | N | A  | 20 | Light ash chestnut |
| T17 | 17 | 100 | $H_2O_2$(20 vol.) | 50  | N | A  | 20 | Metallic grey with blue glints |
| T18 | 18 | 100 | $H_2O_2$(20 vol.) | 100 | N | A  | 25 | Very luminous silver grey with light violet glints |
| T19 | 19 | 100 | $H_2O_2$(20 vol.) | 100 | N | A  | 20 | Silvery grey violet |
| T20 | 20 | 100 | $H_2O_2$(20 vol.) | 100 | N | A  | 20 | Silver blue grey |
| T21 | 21 | 100 | $H_2O_2$(20 vol.) | 100 | D | A  | 20 | Lightly violet dark blue grey |
| T22 | 22 | 100 | $H_2O_2$(20 vol.) | 100 | N | A  | 20 | Deep royal blue |
| T23 | 23 | 100 | $H_2O_2$(20 vol.) | 100 | N | A  | 20 | Copper red |
| T24 | 24 | 100 | $H_2O_2$(20 vol.) | 100 | N | A  | 20 | Silvery mauve blue |
| T25 | 25 | 100 | $H_2O_2$(20 vol.) | 100 | N | A  | 15 | Slight violet reddish chestnut |
| T26 | 26 | 100 | $H_2O_2$(20 vol.) | 100 | N | 30 | 25 | Dark violet |
| T27 | 27 | 100 | $H_2O_2$(20 vol.) | 100 | N | A  | 10 | Deep mahogany |
| T28 | 28 | 100 | $H_2O_2$(20 vol.) | 100 | N | 25 | 20 | Night blue |
| T29 | 29 | 100 | $H_2O_2$(20 vol.) | 100 | N | A  | 20 | Light silvery turquoise blue |
| T30 | 30 | 100 | $H_2O_2$(20 vol.) | 100 | N | 35 | 25 | Hazel |
| T31 | 31 | 100 | $H_2O_2$(20 vol.) | 100 | N | A  | 20 | Slightly violet deep beige |
| T32 | 32 | 100 | $H_2O_2$(20 vol.) | 40  | N | A  | 20 | Steel blue grey |
| T33 | 33 | 100 | $H_2O_2$(20 vol.) | 100 | N | 35 | 20 | Smoke grey |
| T34 | 34 | 100 | $H_2O_2$(20 vol.) | 100 | N | 30 | 25 | Extremely dark grey |
| T35 | 35 | 100 | $H_2O_2$(20 vol.) | 100 | N | A  | 20 | Chestnut with very light eggplant glints |
| T36 | 36 | 100 | $H_2O_2$(20 vol.) | 100 | N | 25 | 20 | Ash blonde |
| T37 | 37 | 100 | $H_2O_2$(20 vol.) | 100 | N | A  | 25 | Deep turquoise blue |
| T38 | 38 | 100 | $H_2O_2$(20 vol.) | 100 | N | 25 | 20 | Royal blue |
| T39 | 39 | 100 | $H_2O_2$(20 vol.) | 100 | N | A  | 30 | Dark violet blue with metallic glints |
| T40 | 40 | 100 | $H_2O_2$(20 vol.) | 100 | N | 25 | 20 | Deep French blue |
| T41 | 41 | 100 | $H_2O_2$(20 vol.) | 50  | N | 30 | 25 | Tin grey with pink glints |
| T42 | 42 | 100 | $H_2O_2$(20 vol.) | 100 | N | A  | 25 | Deep rosewood |
| T43 | 43 | 100 | $H_2O_2$(20 vol.) | 35  | N | 35 | 25 | Light golden chestnut |
| T44 | 44 | 100 | $H_2O_2$(20 vol.) | 75  | N | A  | 20 | Grey blue |
| T45 | 45 | 100 | $H_2O_2$(20 vol.) | 80  | N | A  | 20 | Very strong blue violet |
| T46 | 46 | 100 | Urea peroxide (10% in water) | 100 | N | A | 20 | Metallic grey |
| T47 | 47 | 100 | $H_2O_2$(20 vol.) | 80  | N | 30 | 25 | Deep ash beige |
| T48 | 48 | 100 | $H_2O_2$(20 vol.) | 40  | N | A  | 20 | Very deep French blue |
| T49 | 49 | 100 | $H_2O_2$(20 vol.) | 80  | N | A  | 25 | Light copper pink |
| T50 | 50 | 100 | $H_2O_2$(20 vol.) | 20  | D | A  | 15 | Silvery glycine |
| T51 | 51 | 100 | $H_2O_2$(20 vol.) | 100 | N | A  | 20 | Very deep turquoise blue |
| T52 | 52 | 100 | $H_2O_2$(20 vol.) | 100 | N | A  | 20 | Smoke grey |
| T53 | 53 | 100 | $H_2O_2$(20 vol.) | 45  | N | A  | 20 | Pearly pink beige |
| T54 | 54 | 100 | Urea peroxide (10 wt. % soln.) | 100 | N | A | 15 | Silvery lavender |
| T55 | 55 | 100 | $H_2O_2$(20 vol.) | 100 | N | 35 | 20 | Silvery light mauve grey |
| T56 | 56 | 100 | $H_2O_2$(20 vol.) | 100 | N | A  | 20 | Anthracite grey |
| T57 | 57 | 100 | $H_2O_2$(20 vol.) | 100 | N | A  | 20 | Chestnut |
| T58 | 58 | 100 | $H_2O_2$(20 vol.) | 2   | D | A  | 25 | Pearly very light grey |
| T59 | 59 | 100 | $H_2O_2$(20 vol.) | 100 | D | A  | 20 | Dark French blue |
| T60 | 60 | 100 | $H_2O_2$(20 vol.) | 100 | N | A  | 20 | Very silvery grey |

TABLE E-continued

| | | | | | | | | | |
|---|---|---|---|---|---|---|---|---|---|
| T61 | 61 | 100 | H$_2$O$_2$(20 vol.) | 100 | N | A | | 10 | Very pearly light pink grey beige |
| T62 | 62 | 100 | H$_2$O$_2$(20 vol.) | 30 | N | | 30 | 20 | Deep ash grey with light pink glints |
| T63 | 63 | 100 | H$_2$O$_2$(20 vol.) | 100 | N | A | | 20 | Rosewood |
| T64 | 64 | 100 | H$_2$O$_2$(20 vol.) | 100 | N | A | | 20 | Dark grey |
| T65 | 65 | 100 | H$_2$O$_2$(20 vol.) | 100 | N | A | | 20 | Dark petroleum blue |
| T66 | 66 | 100 | H$_2$O$_2$(20 vol.) | 50 | N | A | | 15 | Silvery eucalyptus green |
| T67 | 67 | 100 | H$_2$O$_2$(20 vol.) | 100 | N | A | | 20 | Silvery almond green |
| T68 | 68 | 100 | H$_2$O$_2$(20 vol.) | 100 | D | A | | 10 | Duck blue |
| T69 | 69 | 100 | H$_2$O$_2$(20 vol.) | 50 | N | A | | 20 | Petroleum blue |
| T70 | 70 | 100 | H$_2$O$_2$(20 vol.) | 80 | N | | 30 | 25 | Fawn |
| T71 | 71 | 100 | H$_2$O$_2$(20 vol.) | 100 | N | | 30 | 25 | Dark grey with mordore glints |
| T72 | 72 | 100 | H$_2$O$_2$(20 vol.) | 100 | N | A | | 25 | Light grey beige |
| T73 | 73 | 100 | H$_2$O$_2$(20 vol.) | 50 | N | | 35 | 25 | Hazel with light pink glints |
| T74 | 74 | 100 | H$_2$O$_2$(20 vol.) | 25 | N | A | | 20 | Bronze green |
| T75 | 75 | 100 | NH$_4$ Persulfate (2.28% in H$_2$O) | 50 | N | | 35 | 30 | Eucalyptus green |
| T76 | 76 | 100 | NH$_4$ Persulfate (2.28% in H$_2$O) | 30 | D | | 35 | 5 | Light bluish silver grey |
| T77 | 77 | 100 | NH$_4$ Persulfate (2.28% in H$_2$O) | 30 | D | A | | 10 | Golden honey |
| T78 | 78 | 100 | H$_2$O$_2$(20 vol.) | 100 | N | A | | 20 | Beige grey |
| T79 | 79 | 200 | H$_2$O$_2$(20 vol.) | 50 | D | A | | 15 + 3 | Lavender blue |

LEGEND OF TABLE E
H$_2$O$_2$(20 vol.) = aqueous solution containing 6 wt. % H$_2$O$_2$
D = bleached hair; N = 95% naturally white hair; A = ambient temperature To facilitate a good understanding of Tables D and E, the following Examples are indicated hereafter in a complete fashion. These Examples are designated only by their number in Table D, but they include each in the last paragraph, the Example of the corresponding dyeing, i.e. they describe first the composition in column (31) of Table D and then the process of dyeing in accordance with the other columns of Table E.

Examples of Composition and Process of Dyeing

EXAMPLE No. 2

Use of compound II as a direct dye
The following dye composition is prepared:

| | |
|---|---|
| Dye of Example II | 0.2 g |
| Ethyl alcohol (96° titer) | 25 g |
| Carboxymethylcellulose | 3 g |
| Ammonia (22° Bé) q.s.p. pH = 10 | |
| Water, q.s.p. | 100 g |

This dye composition is applied for 20 minutes at ambient temperature to bleached hair and imparts thereto, after rinsing and shampooing, a eglantine pink coloration.

EXAMPLE No. 4

The following dye composition containing only direct dyes is prepared.

| | |
|---|---|
| Dye of Example No. IV | 0.7 g |
| (4-nitro-5-N-methylamino)phenyl carboxymethyl ether | 0.5 g |
| 3-nitro-4-N'-methylamino-N,N-methyl, β-hydroxyethylaniline | 1 g |
| Tetraamino anthraquinone | 0.5 g |
| Butyl glycol | 25 g |
| Carboxymethylcellulose | 3.75 g |
| Ammonia (22° Bé) q.s.p. pH = 9.5 | |
| Water, q.s.p. | 100 g |

This dye composition when applied for 25 minutes at ambient temperature to 95% naturally white hair imparts thereto after rinsing and shampooing a silver grey color having light mauve glints.

EXAMPLE NO. 6

The following dye composition is prepared:

| | |
|---|---|
| Dye of Example No. VI | 2 g |
| Lauryl alcohol oxyethylenated with 10.5 moles of ethylene oxide | 20 g |
| Water, q.s.p. | 100 g |
| Ammonia (22° Bé) q.s.p. | pH = 9 |

This dye composition when applied for 20 minutes at 35° C. to bleached hair, imparts thereto after rinsing and shampooing a pink apricot color.

EXAMPLE NO. 9

The following dye composition is prepared wherein Compound No. I plays both the role of the direct dye and of the coupler:

| | | |
|---|---|---|
| Dye of Example No. 1 | 2.5 | g |
| 6-hydroxyphenomorpholine | 0.3 | g |
| 3-methoxy-4-amino N,N-dimethyl-aniline sulfate | 0.3 | g |
| 2,6-dimethyl-4-amino phenol monohydrate hydrochloride | 1.5 | g |
| Propylene glycol | 30 | g |
| Nonyl phenol oxyethylenated with 4 moles of ethylene oxide | 7 | g |
| Nonyl phenol oxyethylenated with 9 moles of ethylene oxide | | g |
| Water, q.s.p. | 100 | g |
| Ammonia (22° Bé), q.s.p. | pH = 10 | |

At the moment of use, 75 g of H$_2$O$_2$ (20 volumes) are added thereto. This resulting mixture when applied to 95% naturally white hair for 15 minutes at 30° C. imparts thereto after rinsing and shampooing an ash beige coloration.

EXAMPLE NO. 20

The following dye composition is prepared:

| | |
|---|---|
| Dye of Example No. VII | 0.84 g |
| Methoxy paraphenylenediamine dihydrochloride | 0.317 g |

-continued

| | |
|---|---|
| Sodium lauryl sulfate with 19% of the alcohol being oxyethylenated. | 20 g |
| Trilon B | 0.2 g |
| Ammonia (22° Bé) | 10 g |
| Sodium bisulfite (40%) | 1 g |
| Water, q.s.p. | 100 g |

At the moment of use, an equal volume of $H_2O_2$ (20 volumes) is added thereto. The resulting mixture when applied for 20 minutes at ambient temperature to 95% naturally white hair imparts thereto, after rinsing and shampooing, a silvery blue grey coloration.

EXAMPLE NO. 73

The following dye composition is prepared wherein the molar ratio of coupler:base is lower than 1.

| | |
|---|---|
| Dye of Example No. III (4-nitro-5-N-methylamino)phenyl carboxymethyl ether | 0.91 g<br>0.2 g |
| Paratoluylenediamine dihydrochloride | 1.17 g |
| Paraamino phenol | 0.654 g |
| Metaamino phenol | 0.545 g |
| Propylene glycol | 25 g |
| Nonyl phenol oxyethylenated with 4 moles of ethylene oxide | 17.5 g |
| Nonyl phenol oxyethylenated with 9 moles of ethylene oxide | 17.5 g |
| Water, q.s.p. | 100 g |
| Ammonia (22° Bé) q.s.p. | pH = 10 |

At the moment of use, 50 cc of $H_2O_2$ (20 volumes) are added thereto. This resulting dye composition when applied for 25 minutes at 35° C. to 95% naturally white hair imparts thereto after rinsing and shampooing a chestnut coloration with light pink glints.

EXAMPLE NO. 77

The following dye composition is prepared wherein the molar ratio of coupler:base is equal to 1.

| | |
|---|---|
| Dye of Example No. V | 0.84 g |
| Paraamino phenol | 0.436 g |
| Butyl glycol | 20 g |
| Diethanolamides of the fatty acids of copra | 8 g |
| Water, q.s.p. | 100 g |
| Ammonia (22° Bé) | 7 g |
| Final pH - 10.5 | |

Before use 30 g of an aqueous solution of ammonium persulfate at 2.28 g percent by weight are added thereto.

This resulting dye composition is applied to bleached hair for 10 minutes at ambient temperature. After rinsing and shampooing, it imparts thereto a golden honey coloration.

EXAMPLE NO. 79

The following dye mixture (a) is prepared initially:

| | |
|---|---|
| Coupler of Example 1 (0.002 mole) | 0.336 g |
| Ethanol | 40 g |
| Water, q.s.p. | 100 g |

This mixture is applied for 15 minutes at ambient temperature to 95% to naturally white hair, or to previously bleached hair. The hair is then rinsed.

The following mixture (b) is prepared:

| | |
|---|---|
| Methoxy paraphenylenediamine dihydrochloride (0.001 mole) | 0.211 g |
| Sodium lauryl sulfate with 19% of the starting alcohol being oxyethylenated | 20 g |
| Trilon B | 0.2 g |
| Sodium bisulfite (40%) | 1 cc |
| Ammonia (22° Bé) | 10 cc |
| Water, q.s.p. | 100 g |

This compositon has a pH of 10.5. At the moment of use, there is added to this composition a solution (c) containing 50 g of $H_2O_2$ (20 volumes) and the resulting mixture is applied at ambient temperature for 3 minutes to hair having been treated with dye mixture (a). The hair is then rinsed, shampooed, rinsed again and dried.

On previously bleached hair, there is obtained a lavender blue coloration; on naturally white hair, a blue grey coloration.

In each of the aforementioned examples, there can also be applied to the hair, successively, a type (a) solution containing at least one coupler of formula I, optionally in the presence of another coupler, and a type (b) solution containing at least one oxidation base of formula II or a heterocyclic oxidation base. The solutions (a) and (b) can be applied in either order. Further a type (c) solution can be applied either separately after the solutions (a) and (b) or in admixture, completely or partially, with the second of solutions (a) or (b) which is applied, with the proviso that in the case where solution (b) contains an oxidation base which itself develops a color in the presence of an oxidizing agent, solution (a) is applied first.

One can also, at the moment of use, mix the said type (a), (b) and (c) solutions. Further, solution (c) can be previously admixed, completely or partially, to solutions (a) and (b).

TABLE F

This Table which describes representative hair setting lotion compositions and their application includes columns having the following meanings:
- (61) number of the Example of the lotion;
- (62), (63) number of the compound used as the dye, and quantity in grams per 100 grams of lotion;
- (64), (65), (66), (67) these columns, relating to the polymers used, indicate respectively the designation of the polymer, its molecular weight, its viscosity and the weight in grams per 100 grams of lotion;
- (68), (69) these columns indicate, respectively, the designation of the dye and its weight in grams per 100 grams of solution;
- (70) indicates the pH. When no mention is indicated relative to the above pH value, it is obtained by the addition of an ammonia solution;
- (71) nature of the hair treated;
- (72) color obtained

EXAMPLES OF HAIR SETTING LOTIONS

| Lo- | Dye | POLYMER | Hair |
|---|---|---|---|

TABLE F-continued

| tion No. (61) | No. (62) | Wt. g % (63) | Name (64) | M.W. (65) | Cps (66) | Wt. g % (67) | Solvents Name (68) | g % (69) | pH (70) | Treated (71) | Coloration (72) |
|---|---|---|---|---|---|---|---|---|---|---|---|
| L1 | IX | 0.5 | Polymer of 80.5% vinyl acetate, 15% allyl stearate, 4.5% allyloxyacetic acid | | | 2.5 | ET | 50 | 8.5 | D | Very lively orange pink |
| L2 | VIII | 0.45 | Polyvinylpyrrolidone sold under the name "K 30" by General Aniline & Film Corporation | 40,000 | | 2 | IP | 35 | 8 | D | Coral |
| L3 | XVI | 0.35 | K 30 | 40,000 | | 2 | IP | 25 | 7.5 TEA | D | Deep pearly turquoise blue |
| L4 | XIII | 0.1 | Copolymer of 60% polyvinylpyrrolidone, 40% vinyl acetate sold under the name "PVP/VA S630" by General Aniline & Film Corporation | | 3.3 to 4 | 2 | IP | 35 | 10 | D | Pearly grey |
| L5 | X | 1.0 | Copolymer of 90% vinyl acetate and 10% crotonic acid | 45,000 to 50,000 | | 1 | ET | 36 | 9 TEA | D | Deep blue grey |
| L6 | XV | 0.3 | Copolymer of 90% vinyl acetate and 10% crotonic acid | 45,000 to 50,000 | | 2 | ET | 50 | 8.5 | D | Beige shaded violet pink |
| L7 | XVIII | 0.2 | Quaternized copolymer of polyvinylpyrrolidone in a 50% solution in alcohol sold under the name "GAFQUAT 734" by General Aniline FRANCE | 100,000 | | 2 | IP | 20 | 5.5 AA | D | Silvery mauve |
| L8 | XII | 0.05 | K 30 | 40,000 | | 2 | IP | 25 | 7.5 TEA | D | Emerald green |
| L9 | XIX | 0.65 | Polymer of 30% polyvinylpyrrolidone, 70% vinyl acetate sold under the name "PVP/VA E 335" by General Aniline & Film Corporation | 160,000 | | 2 | ET | 40 | 8 | D | Very strong blue |
| L10 | XVII | 0.2 | Terpolymer of 20.15% methyl methacrylate, 22.35% stearyl methacrylate, 57.50% dimethylaminoethyl methacrylate completely quaternized with dimethyl sulfate | | 8-12* | 2.5 | ET | 30 | 8 | D | Pearly emerald green |
| L11 | XI | 0.1 | Polymer of 70% polyvinylpyrrolidone, 30% vinyl acetate sold under the name "PVP/VA E 735" by General Aniline & Film Corporation | 40,000 | | 3 | ET | 25 | 10 | D | Silvery light blue |
| L12 | XIV | 0.045 | Butyl Monoester of the copolymer of maleic anhydride methylvinylether sold under the name "GANTREZ EX 435" by General Aniline & film Corporation | 50,000 | | 1 | ET | 45 | 6.8 TEA | D | Pearly pastel blue |
| L13 | IX XVII CD6 | 0.2 0.2 0.05 | PVP/VA E 335 | 160,000 | | 2 | ET | 40 | 9 | D | Rosewood |

LEGEND OF TABLE F
ET = ethanol;
CD6 = N-[(4'-amino)phenyl]2-methyl-5-amino-benzoquinoneimine;
IP = isopropanol;
TEA = triethanolamine;
AA = acetic acid
*determined for a 5% solution in dimethylformamide at the boiling temperature, ether The following Examples are given to provide a good and complete understanding of this aspect of the present invention.

EXAMPLE L2

The following dyeing and hair-setting lotion is prepared:

| | |
|---|---|
| Dye of Example VIII | 0.45 g |
| Polyvinylpyrrolidone sold under the mark "K30" | 2 g |
| Isopropanol | 35 g |
| Water, q.s.p. | 100 g |
| Ammonia (22° Bé) q.s.p. | pH 8 |

This dye composition when applied as a hair-setting lotion to bleached hair imparts thereto a coral coloration.

EXAMPLE L12

The following dyeing and hair-setting lotion is prepared:

| | |
|---|---|
| Dye of Example XIV Butyl monoester of the copolymer of malic anhydride and methyl vinyl ether sold under the mark "Gantrez ES 435". | 0.045 g 1 g |
| Ethyl alcohol (96° titer) | 45 g |
| Water, q.s.p. | 100 g |
| Triethanolamine (20% solution) q.s.p. | pH 6.8 |

This dye composition when applied as a hair-setting lotion to bleached hair imparts thereto a pearly pastel blue coloration.

EXAMPLE L13

The following dyeing and hair-setting lotion is prepared:

| | |
|---|---|
| Dye of Example IX | 0.2 g |
| Dye of Example XVII | 0.2 g |
| N-[(4'-amino)phenyl]-2-methyl-5-amino benzoquinoneimine | 0.05 g |
| copolymer of 30% polyvinyl-pyrrolidone - 70% vinyl acetate, sold under the mark PVP/VA E 335 | 2 g |
| Ethyl alcohol (96° titer) | 40 g |
| Water, q.s.p. | 100 g |
| Ammonia (22° Bé), q.s.p. | pH 9 |

This dye composition when applied as a hair-setting lotion to bleached hair imparts thereto a rosewood coloration.

What is claimed is:

1. An oxidation dye composition for dyeing keratinic fibers comprising in an aqueous medium at least one coupler of the formula

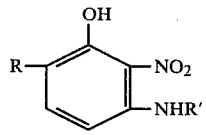

wherein:
R is hydrogen, alkyl or halogen; and
R' is hydrogen, alkyl, hydroxyalkyl, piperidinoalkyl, acetyl or carbethoxy, said coupler being present in an amount of 0.002 to 2 weight percent of said composition, and at least one oxidation base selected from the group consisting of (a) an oxidation base having the formula

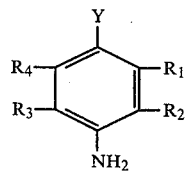

wherein $R_1$, $R_2$, $R_3$ and $R_4$ each independently are selected from the group consisting of hydrogen, alkyl, halogen and alkoxy; and
Y is selected from the group consisting of hydroxyl and $-NR_5R_6$ wherein $R_5$ and $R_6$ each independently are selected from the group consisting of hydrogen, alkyl, hydroxyalkyl, carbamylalkyl, mesylaminoalkyl, aminoalkyl, acylaminoalkyl, sulfoalkyl, morpholinoalkyl and piperidinoalkyl, the said alkyl radicals containing 1-4 carbon atoms; and (b) a heterocyclic compound selected from the group consisting of 2,5-diamino pyridine and 2-hydroxy-5-amino pyridine; the said oxidation base being in the form of the free base or in the form of an acid addition salt thereof, said oxidation base being present in an amount up to 2 weight percent based on the total weight of said composition.

2. The dye composition of claim 1 wherein said aqueous medium is a hydroalcoholic solution containing an alkanol or a glycol in an amount up to 40 weight percent.

3. The dye composition of claim 1 which also includes a cationic, anionic or amphoteric surface active agent in an amount up to 20 weight percent.

4. The composition of claim 1 wherein Y in the compound of formula II is hydroxyl.

5. The composition of claim 1 wherein Y in the compound of formula II is $-NR_5R_6$ wherein $R_5$ and $R_6$ have the meanings given in claim 1.

6. The composition of claim 1 wherein the molar ratio of coupler to oxidation base is 1:5 to 5:1.

7. The composition of claim 1 wherein the molar ratio of coupler to oxidation base is greater than 1.

8. A process for dyeing keratinic fibers comprising successively applying to the said fibers (a) an effective amount of an aqueous solution or hydroalcoholic solution, wherein the alcoholic component comprises 1 to 40 weight percent of the solution,
of as a coupler at least one compound having the formula

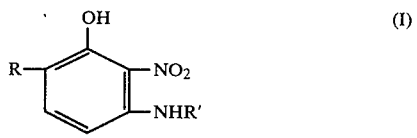

wherein:
R is hydrogen, alkyl or halogen; and
R' is hydrogen, alkyl, hydroxyalkyl, piperidinoalkyl, acetyl or carbethoxy;

(b) an effective amount of an aqueous or hydroalcoholic solution, wherein the alcoholic component comprises 1 to 40 weight percent of the solution containing at least one oxidation base selected from the group consisting of (i) an oxidation base having the formula

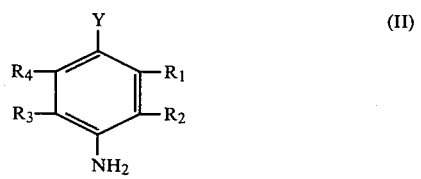

wherein $R_1$, $R_2$, $R_3$ and $R_4$ each independently are selected from the group consisting of hydrogen, alkyl, halogen and alkoxy; Y is selected from the group consisting of hydroxyl and $-NR_5R_6$ wherein $R_5$ and $R_6$ each independently are selected from the group consisting of hydrogen, alkyl, hydroxyalkyl, carbamylalkyl, mesylaminoalkyl, aminoalkyl, acylaminoalkyl, sulfoalkyl, morpholinoalkyl and piperidinoalkyl, the said alkyl radicals containing 1-4 carbon atoms, and (ii) a heterocyclic compound selected from the group consisting of 2,5-diaminopyridine and 2-hydroxy-5-amino-pyridine, said oxidation base being in the form of the free base or in the form of an acid addition salt thereof; and (c) an effective amount of an aqueous or hydroalcoholic solution, wherein the alcoholic component is 1 to 40 weight percent of the solution, containing an oxidizing agent, said solution (c) being applied either separately after solutions (a) and (b), or totally or in admixture with the second of said solutions (a) or (b) to be applied; with the proviso that where solution (b) contains an oxidation base which itself develops a color in the presence of an oxidizing agent, solution (a) is applied first.

9. The process of claim 8 wherein solution (a) also includes another coupler.

10. A process for dyeing keratinic fibers comprising applying to said fibers an effective amount of an oxidation hair dye composition comprising an aqueous or hydroalcoholic solution, wherein the alcoholic component is 1 to 40 weight percent of said solution, of a mixture of (a) at least one coupler having the formula

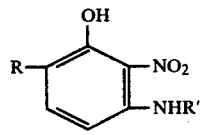

wherein R is hydrogen, alkyl or halogen; and R' is hydrogen, alkyl, hydroxyalkyl, piperidinoalkyl, acetyl or carbethoxy; (b) at least one oxidation base selected from the group consisting of (i) an oxidation base having the formula

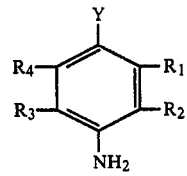

wherein $R_1$, $R_2$, $R_3$ and $R_4$ each independently are selected from the group consisting of hydrogen, alkyl, halogen and alkoxy; and Y is selected from the group consisting of hydroxyl and $-NR_5R_6$ wherein $R_5$ and $R_6$ each independently are selected from the group consisting of hydrogen, alkyl, hydroxyalkyl, carbamylalkyl, mesylaminoalkyl, aminoalkyl, acylaminoalkyl, sulfoalkyl, morpholinoalkyl and piperidinoalkyl, the said alkyl radicals containing 1-4 carbon atoms, and (ii) a heterocyclic compound selected from the group consisting of 2,5-diamino pyridine and 2-hydroxy-5-amino pyridine, said oxidation base being in the form of the free base or in the form of an acid addition salt thereof; and (c) an oxidizing agent, said components (a) and (b) being admixed at a point in time just before said fibers are dyed and component (c) being admixed with the resulting mixture of components (a) and (b) or with either of components (a) and (b) prior to admixture of components (a) and (b).

11. The process of claim 10 which includes permitting the admixture of components (a), (b) and (c) to remain in contact with said fibers for a period of time ranging from 10 minutes to 30 minutes and thereafter rinsing the said fibers, shampooing the said fibers and drying the said fibers.

* * * * *

UNITED STATES PATENT AND TRADEMARK OFFICE
CERTIFICATE OF CORRECTION

PATENT NO. : 4,330,291
DATED : May 18, 1982
INVENTOR(S) : Andree BUGAUT and Ginette JEANMINET It is certified that error appears in the above—identified patent and that said Letters Patent is hereby corrected as shown below:

On the title page

Please add the following

-- [73] Assignee: Societe Anonyme dite: L'OREAL, Paris, France --

*Signed and Sealed this*

*Fourteenth* Day of *September 1982*

[SEAL]

*Attest:*

*Attesting Officer*

GERALD J. MOSSINGHOFF
*Commissioner of Patents and Trademarks*